US009822399B2

(12) United States Patent
Saito et al.

(10) Patent No.: US 9,822,399 B2
(45) Date of Patent: Nov. 21, 2017

(54) METHOD FOR ANALYZING BIOMOLECULES AND BIOMOLECULE ANALYZER

(71) Applicant: HITACHI HIGH-TECHNOLOGIES CORPORATION, Tokyo (JP)

(72) Inventors: Toshiro Saito, Tokyo (JP); Koshin Hamasaki, Tokyo (JP); Satoshi Takahashi, Tokyo (JP); Muneo Maeshima, Tokyo (JP); Kyoko Imai, Tokyo (JP); Kazumichi Imai, Tokyo (JP); Ryuji Tao, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

(21) Appl. No.: 14/349,520

(22) PCT Filed: Oct. 4, 2012

(86) PCT No.: PCT/JP2012/075807
§ 371 (c)(1),
(2) Date: Apr. 3, 2014

(87) PCT Pub. No.: WO2013/051651
PCT Pub. Date: Apr. 11, 2013

(65) Prior Publication Data
US 2014/0295430 A1 Oct. 2, 2014

(30) Foreign Application Priority Data

Oct. 5, 2011 (JP) .................................. 2011-221024
Oct. 27, 2011 (JP) .................................. 2011-236138

(51) Int. Cl.
*C12Q 1/68* (2006.01)
*G01N 21/64* (2006.01)
(Continued)

(52) U.S. Cl.
CPC ......... *C12Q 1/6834* (2013.01); *C12Q 1/6804* (2013.01); *C12Q 1/6837* (2013.01);
(Continued)

(58) Field of Classification Search
CPC ..... C12Q 1/68; C12Q 1/6837; G01N 21/6428
See application file for complete search history.

(56) References Cited

U.S. PATENT DOCUMENTS 7,682,837 B2 * 3/2010 Jain ........................ B03C 1/035
427/128
2003/0040129 A1 * 2/2003 Shah ..................... B01L 3/5027
506/32
(Continued)

FOREIGN PATENT DOCUMENTS

JP WO 2010/087121 * 8/2010
JP WO2010/092958 * 8/2010
(Continued)

OTHER PUBLICATIONS

Xue et al, Quantitative Detection of Single Molecules Using Enhancement of Dye/DNA Conjugate-Labeled Nanoparticles, 2010, Bioconjugate Chem., 21, 1987-1993.*
(Continued)

*Primary Examiner* — Narayan Bhat
(74) *Attorney, Agent, or Firm* — Mattingly & Malur, PC

(57) ABSTRACT

The method for analyzing biomolecules, includes the steps of: immobilizing biomolecules to be analyzed on surfaces of magnetic microparticles; reacting labeled probe molecules with the biomolecules to be analyzed; collecting and immobilizing the microparticles on a support substrate; and measuring a label on the support substrate. Since single-molecule immobilized magnetic microparticles are used in the present invention, the number of biomolecules can be counted, and since hybridization and an antigen-antibody
(Continued)

reaction are performed with the microparticles having biomolecules immobilized thereon dispersed, the reaction can be rapidly performed. Further, the type and the abundance of biomolecules of interest can be determined at a single molecular level, so as to evaluate, in particular, the absolute concentration of biomolecules.

17 Claims, 10 Drawing Sheets

(51) Int. Cl.
    *G01N 33/543*     (2006.01)
    *G01N 33/58*     (2006.01)

(52) U.S. Cl.
    CPC ..... *G01N 21/6428* (2013.01); *G01N 21/6452* (2013.01); *G01N 33/54326* (2013.01); *G01N 33/54346* (2013.01); *G01N 33/54393* (2013.01); *G01N 33/587* (2013.01); *G01N 2021/6421* (2013.01)

(56) References Cited

U.S. PATENT DOCUMENTS

| | | | |
|---|---|---|---|
| 2010/0009862 A1* | 1/2010 | Nakahara | G01N 21/6428 506/9 |
| 2011/0025315 A1 | 2/2011 | Ohtsuka | |
| 2011/0281320 A1* | 11/2011 | Saito | C12Q 1/6816 435/176 |
| 2011/0287446 A1* | 11/2011 | Kanda et al. | 435/7.1 |

FOREIGN PATENT DOCUMENTS

| | | |
|---|---|---|
| JP | 2011-033454 A | 2/2011 |
| WO | 2004/027093 A1 | 4/2004 |
| WO | WO2008/116093 * | 9/2008 |
| WO | 2011/109364 A2 | 9/2011 |

OTHER PUBLICATIONS

Cannon et al, Zeptomole detection of DNA nanoparticles by single-molecule fluorescence with magnetic field-directed localization, 2012, Analytical Biochemistry, 431, 40-47.*
European Search Report received in corresponding European Application No. 12838806 dated Feb. 3, 2015.
D. Thieme et al: "Sandwich Hybridization Assay for Sensitive Detection of Dynamic Changes in mRNA Transcript Levels in Crude *Escherichia coli* Cell Extracts in Response to Copper Ions", vol. 74. No. 24, Oct. 24, 2008, pp. 7463-7470.
J. Goransson et al.: "A single molecule array for digital targeted molecular analysis", Nucleic Acids Research, vol. 37, No. 1, Jan. 1, 2009, pp. e7-e7.
Science vol. 270, pp. 467-470, 1995.
Proc. Natl. Acad. Sci., vol. 103, pp. 3687-3692, 2006.
Nature Biotechnology, vol. 28, pp. 595-599, 2010.
Japanese Notification of Opposition Statement received in corresponding Japanese Opposition No. 2016-700447 (now U.S. Pat. No. 5,816,291) dated Jun. 6, 2016.
Yokota, H. et al., "Single Molecule Fluorescence Imaging and Blinking", The Biophysical Society of Japan, 2006, pp. 164-168, vol. 46, No. 3 with partial translation.

* cited by examiner

A

B

METHOD FOR ANALYZING BIOMOLECULES AND BIOMOLECULE ANALYZER

TECHNICAL FIELD

The present invention relates to a method for analyzing biomolecules and a biomolecule analyzer.

BACKGROUND ART

In recent years, a method for simply analyzing the type and the quantity of biomolecules contained in a sample has been developed as a biomolecule analysis method. For example, in a DNA microarray, various types of synthetic DNAs each having a sequence capable of identifying a known gene sequence are immobilized in prescribed positions on a support substrate, a nucleic acid sample labelled with a fluorophore, or a reverse transcript or an amplified product of a nucleic acid sample is hybridized on the support substrate, and then, a fluorescent image is captured by using a fluorescent scanner. Thus, it can be analyzed, based on fluorescent intensity, which gene is expressed at what expression level (Non Patent Literature 1). Further, a method for detecting a specific biomolecule by so-called a sandwich assay (enzyme linked immunosorbent assay: ELISA) in which an antibody specifically binding to a biomolecule to be detected is immobilized on a support substrate, a sample for the analysis is allowed to flow thereon for causing a prescribed specific binding reaction, and then a fluorescent labeled antibody is allowed to flow thereon for performing fluorescence detection has been put to practical use.

In either of the methods, probe molecules which specifically capture the biomolecule to be detected are immobilized in advance on the support substrate, and a sample for the analysis is allowed to flow thereon to cause a prescribed specific binding reaction, so as to perform quantitative analysis by fluorescence measurement or the like.

CITATION LIST

Non Patent Literature

Non Patent Literature 1: Science Vol. 270, pp. 467-470, 1995
Non Patent Literature 2: Proc. Natl. Acad. Sci., Vol. 103, pp. 3687-3692, 2006
Non Patent Literature 3: Nature Biotechnology, Vol. 28, pp. 595-599, 2010

SUMMARY OF INVENTION

Technical Problem

In the conventional analysis methods such as the DNA microarray and the ELISA (enzyme linked immunosorbent assay), a specific binding reaction with fluorescent-labeled (or enzyme-labeled) biomolecules is performed in a reaction site where several tens to tens of thousands probe molecules are immobilized, and thereafter, the number of biomolecules binding to the reaction site is relatively compared by the measurement of fluorescence intensity. The dynamic range is 2 to 3 digits, which is lower than the dynamic range (4 or less digits) of the actual abundance of biomolecules reported (in Non Patent Literature 2).

Furthermore, single-molecule ELISA has been reported. In this method, a plurality of antibodies are immobilized on microparticles, merely one molecule of an antigen contained in a diluted sample is allowed to bind to the antibody per microparticle, the microparticles are collected and immobilized on a support, and a label is measured on the support so as to analyze the biomolecule (antigen) (Non Patent Literature 3). This method is, however, known to have the following disadvantages: Since a plurality of antibodies are immobilized on the microparticles, there is a possibility that two or more molecules of the antigen are bound. If two or more molecules are bound, such multiple binding is difficult to distinguish in the detection. Further, even if microparticles do not enter some holes on the support, this cannot be distinguished in the detection.

Moreover, in the specific binding reaction, the specifically binding probe molecules are immobilized on the support substrate and hence cannot move, and therefore, the reaction time is very long. For example, in employing the DNA microarray, the hybridization takes 10 hours or more, and hence, this method is disadvantageous in that it is difficult to employ the same for example, in a clinical laboratory test where rapid analysis is required.

In addition, although the aforementioned methods can be employed for comparative expression analysis between samples, they basically are not for measuring the absolute number of the biomolecules actually extracted. Therefore, the problem remains that biomolecules which greatly affect the whole cell even when expressed at trace levels can be overlooked due to other biomolecules expressed at high levels.

An object of the present invention is to provide a method and means for analyzing biomolecules that can realize, in biomolecule analysis, a wide dynamic range attained by counting the number of biomolecules and rapid analysis.

Another object of the present invention is, in analysis of biomolecules, in particular, nucleic acid molecules, to provide a simple method for directly analyzing the absolute number of biomolecules, which can comprehensively analyze thousand or more types of biomolecules at a time and can perform type discrimination and quantitative determination of biomolecules at a single molecular level with a dynamic range of 4 digits or more, by capturing biomolecules extracted from a sample and without using amplification reactions such as PCR or the like. The present invention provides an analysis method extremely useful for analyzing biomolecules, in particular, noncoding RNAs and micro RNAs of ten thousands types or less.

Solution to Problem

The present invention relates to a method for analyzing the type and the abundance of biomolecules present in a sample containing the biomolecules. Specifically, the present inventors have found the following and completed the present invention: Biomolecules to be analyzed are immobilized on magnetic microparticles, and with the magnetic microparticles dispersed in a solution, a reaction with probe molecules specifically binding to the biomolecules is performed. After the reaction, the microparticles are collected and immobilized by using magnetic force on a support substrate, so as to be detected and evaluated by fluorescence measurement or the like. Thus, the number of biomolecules can be counted and the reaction can rapidly be performed.

Specifically, the present invention encompasses the following:

[1] A method for analyzing biomolecules, comprising the steps of: immobilizing biomolecules to be analyzed on the surface(s) of magnetic microparticles; reacting labeled probe molecules with the biomolecules to be analyzed; collecting and immobilizing the microparticles on a support substrate; and measuring the label(s) on the support substrate.

[2] The method for analyzing biomolecules according to [1], wherein capture molecules are immobilized in advance on the surfaces of the magnetic microparticles, and then the biomolecules to be analyzed are immobilized on the surfaces of the magnetic microparticles via the capture molecules.

[3] The method for analyzing biomolecules according to [1] or [2], wherein one capture molecule is immobilized in advance on each of the magnetic microparticles, and then the biomolecules to be analyzed are immobilized on the surfaces of the magnetic microparticles via the capture molecules.

[4] The method for analyzing biomolecules according to any one of [1] to [3], wherein one molecule among the biomolecules to be analyzed is immobilized per each of the magnetic microparticles.

[5] The method for analyzing biomolecules according to any one of [1] to [4], wherein the magnetic microparticles are collected and immobilized on the support substrate by using magnetic force.

[6] The method for analyzing biomolecules according to any one of [1] to [5], wherein the step of reacting labeled probe molecules with the biomolecules to be analyzed is performed after the step of immobilizing biomolecules to be analyzed on surfaces of magnetic microparticles.

[7] The method for analyzing biomolecules according to any of [1] to [5], wherein the step of immobilizing biomolecules to be analyzed on surfaces of magnetic microparticles is performed after the step of reacting labeled probe molecules with the biomolecules to be analyzed.

[8] The method for analyzing biomolecules according to any one of [1] to [7], wherein the label(s) is(are) (a) fluorescent label(s).

[9] The method for analyzing biomolecules according to [8], wherein the fluorescent labels are labeled probe molecules with multiple types of fluorophores mixed in different ratios depending on the type(s) of biomolecule(s) to be measured.

[10] The method for analyzing biomolecules according to [8], wherein the fluorescent labels are labeled probe molecules with fluorophores emitting fluorescence in different colors depending on the type(s) of biomolecule(s) to be measured.

[11] The method for analyzing biomolecules according to any one of [8] to [10], wherein the step of measuring the label(s) comprises measuring fluorescence.

[12] The method for analyzing biomolecules according to any one of [1] to [11], further comprising the step of adding a common label to the biomolecules to be analyzed, wherein probe molecules labeled with a label different from the common label are reacted with the biomolecules to be analyzed in order to calculate the ratio between the common label and the different label, and the quantity of reacted biomolecules among the total quantity of the biomolecules to be analyzed is evaluated based on the ratio.

[13] The method for analyzing biomolecules according to any one of [1] to [12], wherein the biomolecules are nucleic acids.

[14] The method for analyzing biomolecules according to [13], wherein the probe molecules are nucleic acids which can hybridize with the biomolecules to be measured.

[15] The method for analyzing biomolecules according to any one of [1] to [12], wherein the biomolecules are proteins.

[16] The method for analyzing biomolecules according to [15], wherein the probe molecules are antibodies to biomolecules to be measured.

[17] A biomolecule analyzer, comprising: means for immobilizing biomolecules to be analyzed on magnetic microparticles; means for reacting labeled probe molecules and the biomolecules to be analyzed; means for collecting and immobilizing the magnetic microparticles on a support substrate after the reaction; and means for measuring a label.

[18] The biomolecule analyzer according to [17], wherein the means for measuring a label comprises light irradiating means and emission detecting means.

[19] A method for analyzing biomolecules, comprising preparing biomolecules to be analyzed; reacting labeled probe molecules with the biomolecules; and detecting the label(s) of the probe molecules bound to the biomolecules, thereby evaluating the absolute concentration of biomolecules of interest.

[20] The method according to [19], further comprising the step of immobilizing the biomolecules to be analyzed, one molecule per position, in positions spatially separated from one another.

[21] The method according to [19] or [20], further comprising the steps of adjusting the concentration of the biomolecules to be analyzed, stirring the biomolecules to be analyzed, and immobilizing the biomolecules to be analyzed, one molecule per position, in positions spatially separated from one another.

[22] The method according to any one of [19] to [21], wherein the biomolecules to be analyzed are immobilized on a support substrate, one molecule per position, in positions spatially separated from one another.

[22-2] The method according to any one of [19] to [21], wherein substantially all of, and preferably all of the biomolecules to be analyzed are immobilized.

[23] The method according to any one of [19] to [22], wherein the biomolecules are nucleic acid molecules, and the probe molecules are nucleic acid molecules having (a) complementary sequence(s) to the biomolecule(s) of interest.

[23-2] The method according to any one of [19] to [22], wherein the biomolecules are proteins, and the probe molecules are antibodies to the biomolecule(s) of interest.

[24] A method for analyzing nucleic acid molecules, wherein biomolecules are nucleic acid molecules, comprising the steps of: immobilizing nucleic acid molecules to be analyzed, one molecule per position, in positions spatially separated from one another; hybridizing, with the nucleic acid molecules to be analyzed, probe nucleic acid molecules each having a known nucleotide sequence and each being labeled; and evaluating, after the step of hybridization, the absolute concentration of nucleic acid molecules of interest by detecting the label.

[25] The method according to [24], further comprising the steps of adjusting the concentration of the nucleic acid molecules to be analyzed, stirring the nucleic acid molecules to be analyzed, and immobilizing the nucleic acid molecules to be analyzed, one molecule per position, in positions spatially separated from one another.

[26] The method according to [24] or [25], wherein the nucleic acid molecules to be analyzed are immobilized on a support substrate, one molecule per position, in positions spatially separated from one another.

[27] The method according to any one of [19] to [26], comprising the step of immobilizing the biomolecules to be analyzed one molecule per microparticle on the microparticles.

[27-2] The method according to [27], wherein one capture molecule is immobilized in advance on each of the microparticles, and the biomolecules to be analyzed are immobilized on the microparticles via the capture molecule.

[28] The method according to any one of [19] to [27], wherein the label(s) is(are) (a) fluorescent label(s).

[29] The method according to any one of [19] to [28], wherein the labels are microparticles containing multiple types of fluorophores mixed in different ratios depending on the type(s) of biomolecule(s) of interest.

[29-2] The method according to any one of [19] to [28], wherein the labels are fluorophores emitting fluorescence of different colors depending on the type(s) of biomolecule(s) of interest.

[29-3] The method according to [28] or [29], wherein detection of the label(s) is detection of fluorescence.

[30] The method according to any one of [19] to [29], wherein an identical label is used for probe molecules for biomolecules other than the biomolecules of interest, the number of labels are counted with respect to each type of biomolecule of interest, and the ratio(s) of the number of labels of each type of biomolecule of interest to the total number of labels is(are) calculated in order to evaluate the absolute concentration(s) of each type of (the) biomolecule(s) of interest.

[31] The method according to any one of [19] to [30], further comprising the step of adding a common label to the biomolecules to be analyzed, wherein the biomolecules to be analyzed are reacted with probe molecules labeled with a label different from the common label, and the ratio in number between number of common label(s) and the number of different label(s) is calculated in order to evaluate the absolute concentration of each type of biomolecule of interest.

[32] The method according to any one of [27] to [31], wherein one of the biomolecules to be analyzed is immobilized on each microparticle, wherein the microparticles are magnetic microparticles, the labels are multiple types of fluorophores mixed in different ratios depending on the type(s) of the biomolecule(s) of interest, and after reacting the biomolecules to be analyzed with the probe molecules, unbound probe molecules and unbound magnetic microparticles are removed, and the label(s) of the probe molecules bound to the biomolecules on the magnetic microparticles is(are) detected.

[33] A biomolecule analyzer, comprising: means for immobilizing biomolecules to be analyzed, one molecule per position, in positions spatially separated from one another; means for reacting labeled probe molecules with the biomolecules; and means for detecting the label of the probe molecules bound to the biomolecules, wherein the absolute concentration of biomolecules of interest is evaluated based on the number of detected labels.

[34] The analyzer according to [33], wherein the means for immobilizing comprises means for adjusting the concentration of the biomolecules to be analyzed; and means for stirring the biomolecules to be analyzed.

[34-2] The analyzer according to [33] or [34], wherein the means for detecting the label comprises light irradiating means and emission detecting means.

Advantageous Effects of Invention

According to the present invention, the abundance of biomolecules can be analyzed by counting the number of molecules with single molecule resolution, and hence, a very large dynamic range is attained. Furthermore, biomolecules immobilized on microparticles are reacted in solution in a dispersed state with probe molecules, and therefore, the binding reaction between the probe molecules and the biomolecules can be performed rapidly. Accordingly, biomolecule analysis can be rapidly carried out with a large dynamic range by the method for analyzing biomolecules and the biomolecule analyzer of the present invention.

Furthermore, according to the present invention, due to the step of adjusting the concentration of a sample and the step of stirring, individual biomolecules can be arranged with high probability respectively in positions spatially separated from one another without losing the extracted sample at all, and the biomolecules can be simply and rapidly analyzed with single molecule sensitivity and resolution and with high comprehensiveness and quantitativeness. Moreover, as compared with conventional methods, the sensitivity is very high and there is no amplification bias in the present invention, and therefore, the abundance, in cells, of biomolecules to be analyzed can be evaluated in a state very close to the actual state.

Further, in a biomolecule sample composed of multiple types of biomolecules, each of the biomolecules to be analyzed is immobilized in each of the immobilization positions with regularity on a support substrate, and probe molecules known to bind to biomolecules of interest are reacted with the biomolecules immobilized on the support substrate, so as to detect the probe molecules. Accordingly, the type and abundance of biomolecules being analyzed can be simply and rapidly analyzed with both comprehensiveness and quantitativeness and with single molecule sensitivity and resolution.

Problems, configurations and effects apart from those described above will be apparent from the description of the embodiments below.

DESCRIPTION OF EMBODIMENTS

Figure 1:
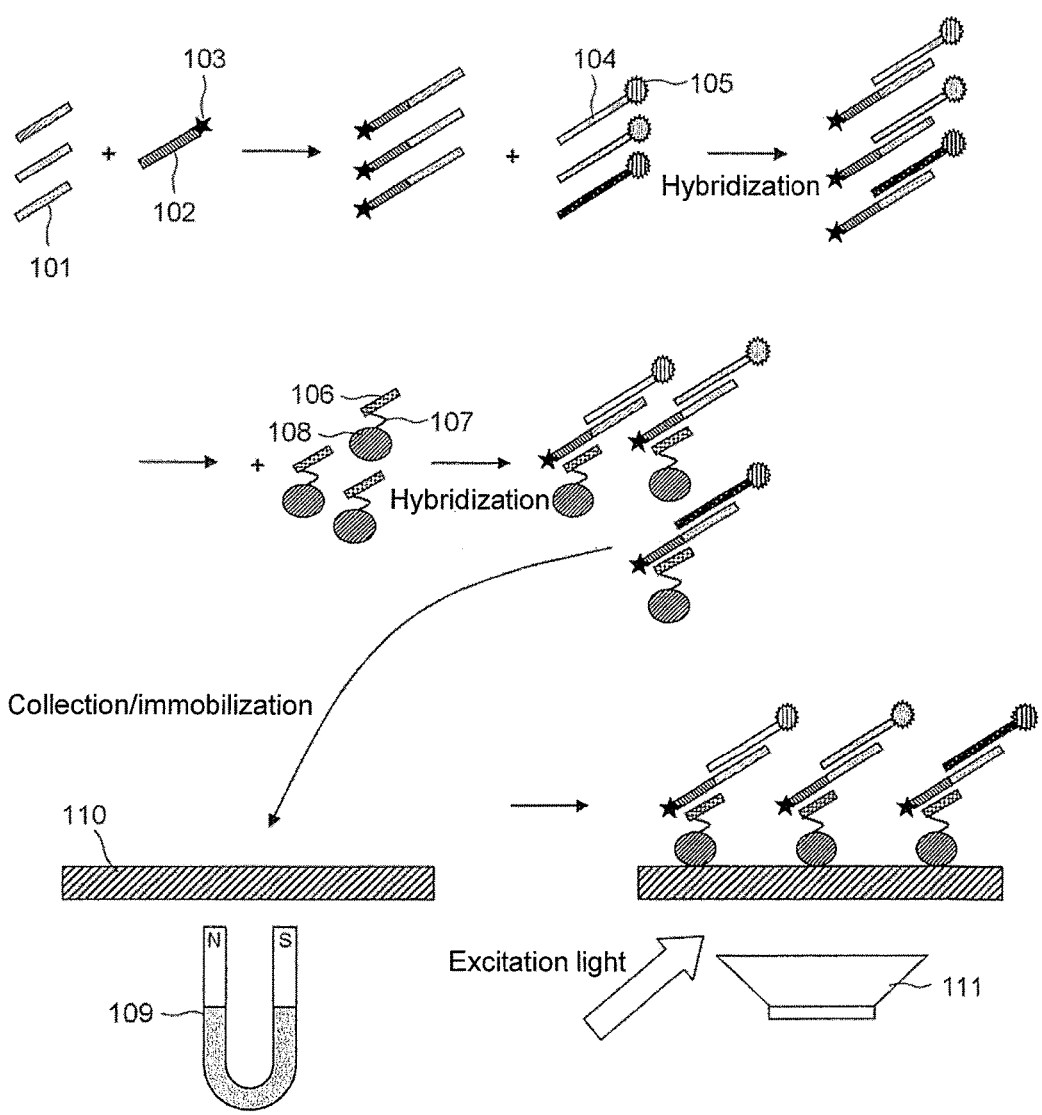
FIG. 1 is a diagram illustrating an exemplified analysis method of one example.

The present invention relates to a method for analyzing biomolecules by reacting biomolecules to be analyzed and probe molecules specifically binding to biomolecules to be analyzed, and in this method, biomolecules to be analyzed are immobilized on magnetic microparticles and the magnetic microparticles are simply and rapidly collected and immobilized on a support substrate, so as to detect the reaction. Further, each of the biomolecules to be analyzed is immobilized on each microparticle, so as to analyze the biomolecules with high accuracy and a high dynamic range. Furthermore, the individual biomolecules to be analyzed are immobilized respectively in positions spatially separated from one another, so as to evaluate the absolute concentration of biomolecules of interest with high comprehensiveness and a high dynamic range.

The biomolecule to be analyzed is not particularly limited as long as it is a molecule from a living organism desired to be analyzed regarding the type, the expression level or the abundance, the presence, or the like thereof. Examples include nucleic acids (such as messenger RNAs (mRNAs), non-coding RNAs (ncRNAs), micro RNAs, DNAs, and aptamers) and fragments thereof, proteins (such as peptides, polypeptides and antibodies) and fragments thereof, and sugars. Incidentally, the biomolecule includes a polymer having a sequence or a constituent not existing in nature, and includes an artificially synthesized biomolecule having, for example, a poly(A), poly(T), poly(G), poly(C) or arbitrary sequence. Further, the biomolecule includes a nucleic acid prepared by a nucleic acid amplification method known in the art (such as polymerase chain reaction), and a nucleic acid cloned into a vector.

Furthermore, the origin of the biomolecule to be analyzed is not particularly limited, and the biomolecule can be derived from any sample of a cell sample, a tissue sample, a liquid sample or the like of any organism such as a vertebrate (such as a mammal, a bird, a reptile, fish or an amphibia), an invertebrate (such as an insect, a nematode or a crustacean), a protist, a plant, a fungus, a bacteria or a virus. Specific examples include a sample containing one cell, a sample containing a plurality of cells, and a tissue section sample. Alternatively, the biomolecule may be derived from an artificial source such as a DNA library, an antibody library or a peptide library.

A method for preparing the biomolecule to be analyzed from the sample is known in the art. For example, cells can be lysed by using a protease such as Proteinase K, a chaotropic salt such as guanidine thiocyanate or guanidine hydrochloride, a surfactant such as Tween or SDS, or a commercially available cell lysis agent, so as to elute nucleic acids, namely, DNAs and RNAs, contained in the cells. If RNAs (such as mRNAs) are used as the biomolecules to be analyzed, among nucleic acids eluted by the aforementioned cell lysis, DNAs are lysed by using a deoxyribonuclease (DNase), so as to obtain a sample containing RNAs alone as the nucleic acids.

A common label may be added to the biomolecules to be analyzed, and in this case, the number or the quantity of the biomolecules to be analyzed can be measured by measuring the common label in a label measuring step described hereinbelow. The common label is different from a label to be added to probe molecules described hereinbelow so that it can be identified in the label measuring step. As the common label, any label known in the art can be used, and examples include fluorescent labels (such as Cy3, Cy5, fluorescein isothiocyanate (FITC) and tetramethylrhodamine isothiocyanate (TRITC)), a luminescent semiconductor label (such as zinc selenide (Zn—Se)), a chemiluminescent label (such as luciferin), an enzyme label (such as peroxidase, β-galactosidase, or alkaline phosphatase), and a radioactive label (such as tritium or iodine-125). The label is preferably a fluorescent label, by taking into consideration the readiness of measurement in the label measuring step described hereinbelow.

A method for adding the label to the biomolecules to be analyzed is not particularly limited, and a method known in the art may be employed. For example, the label may be directly bound to the biomolecules, the biomolecules and the label may be bound to each other via a suitable linker (such as a capture tag used in Example 1), or the biomolecules may be bound, via a primary antibody, to the label as a secondary or tertiary antibody.

The probe molecule is not particularly limited as long as it can specifically bind to the biomolecule to be analyzed, and depends upon the type of biomolecule to be analyzed or a biomolecule to be measured. If the biomolecules to be analyzed are nucleic acids, a nucleic acid capable of hybridizing with a biomolecule to be measured, such as a nucleic acid having a sequence complementary to the sequence of the biomolecule, can be used as the probe molecule. Methods for designing and preparing a probe molecule hybridizing with a biomolecule (nucleic acid) are known in the art, and a suitable molecule can be designed to have a length of approximately 10 to 60 bases by considering melting temperature (Tm) and GC content. Further, there is a known program to be used for designing such a molecule.

Further, if the biomolecule to be analyzed is a protein, an antibody (including a whole antibody, an antibody fragment, a domain antibody, and the like) specific to the protein to be measured, an aptamer nucleic acid or the like can be used as the probe molecule. If the biomolecule to be analyzed is an antibody (such as a serum antibody), an antigen (such as a peptide or a sugar) to which an antibody to be measured is bound, then an antibody binding to the antibody to be measured, or the like can be used as the probe molecule. If the biomolecule to be analyzed is a sugar or glycoprotein, then lectin or the like can be used as the probe molecule. In either case, those skilled in the art can design and prepare a suitable probe molecule based on the biomolecule to be measured.

The probe molecules may be of one type or a plurality of types. The probe molecules are prepared in accordance with the type of biomolecules to be measured.

The probe molecule is labeled with a suitable label. The type of the label and the method for adding the label are appropriately selected in the same manner as described above. If multiple types of probe molecules are used for correspondingly measuring multiple types of biomolecules, then different labels are preferably used so as to identify the multiple types. For example, multiple types of fluorophores mixed in different ratios may be used depending on (respectively corresponding to) the multiple types of biomolecules, or fluorophores emitting fluorescence of different colors may be used depending on the multiple types of biomolecules, so that the probe molecules can be identifiably labeled.

The reaction which occurs between the biomolecules to be analyzed and the labeled probe molecules depends upon the types of the biomolecules and the probe molecules, and can be performed in accordance with a method known in the art. For example, if the biomolecules to be analyzed are nucleic acids, a hybridization reaction with probe molecules (nucleic acids) can be performed. The hybridization reaction is carried out by incubating, in a solid phase system or a liquid phase system under stringent conditions, biomolecules to be analyzed (nucleic acids) immobilized or not immobilized on magnetic microparticles and probe molecules (nucleic acids). The stringent conditions are well known in the art, and those skilled in the art can select appropriate stringent conditions. Further, after the hybridization reaction, residual reagents and unbound molecules are preferably removed by washing.

If the biomolecule to be analyzed is a protein or an antibody, a reaction based on an antigen-antibody reaction with an antibody or a protein which specifically binds to the protein or the antibody can be performed. Such reaction is well known in the art, and for example, the reaction can be caused by bringing the biomolecule to be analyzed immobilized or not immobilized on a magnetic microparticle and a probe molecule into contact with each other in a solid phase system or a liquid phase system. Similarly, if the biomolecule to be analyzed is a protein and an aptamer nucleic acid specifically binding to the protein is used as the probe molecule, then the biomolecule and the probe molecule can be bound to each other similarly by bringing them into contact with each other in a solid phase system or a liquid phase system. After the reaction, residual reagents and unbound molecules are preferably removed by washing.

The biomolecule to be analyzed is immobilized on the surface of a magnetic microparticle. Immobilization onto a microparticle may be performed before (as in Example 2, for example) or after (as in Example 1, for example) a step of reacting the labeled probe molecules with the biomolecules to be analyzed.

Further, it is preferable to immobilize the individual biomolecules to be analyzed, one molecule per position, in positions spatially separated from one another. In particular, substantially all of the biomolecules to be analyzed, for example, 90% or more, preferably 95% or more, more preferably 99% or more, and most preferably 100% of said biomolecules to be analyzed are immobilized. For example, the biomolecules to be analyzed can be immobilized on microparticles. The immobilization onto a microparticle may be performed before (as in Example 3, for example) or after (as in Examples 7 and 8, for example) the step of reacting the labeled probe molecules with the biomolecules to be analyzed.

The magnetic microparticle is not particularly limited as long as it is a magnetic microparticle that is magnetized or can be magnetized, and magnetic microparticles usable in the art are commercially available. The magnetic microparticle is a microparticle made of iron oxide such as magnetite (supermagnetic material) or a microparticle produced by coating with a supermagnetic layer, and the diameter thereof is 100 µm or less, preferably 50 µm or less, more preferably 10 µm or less, and for example, 1.0 µm to 10.0 µm. The material and the size of the magnetic microparticle are determined preferably in consideration of dispersibility in a solution, the type of biomolecules to be analyzed, the type of the reaction and the like. Since the magnetic microparticle is used, collection and immobilization onto a support substrate described hereinbelow can be automatically, efficiently or rapidly performed.

Immobilization of the biomolecules to be analyzed onto the magnetic microparticles can be performed by any method known in the art. The biomolecule can be immobilized onto the surface of the microparticle by utilizing, for example, a covalent bond, an ionic bond, physical adsorption, a complementary bond, or a biological bond (such as a bond between biotin and avidin or streptavidin, or a bond between an antigen and an antibody). Alternatively, the biomolecule can be immobilized on the magnetic microparticle via another molecule (such as a capture tag or a capture molecule used in Example 1 or 3). Incidentally, other molecules to be bound respectively to the biomolecule to be analyzed and the magnetic microparticle are herein designated respectively as a "capture tag" and a "capture molecule" for convenience, and both of these, one of these or none of these may be used. Specifically, for example, with a capture molecule immobilized in advance on the surface of a magnetic microparticle, a biomolecule to be analyzed (or a biomolecule to be analyzed having been bound to a capture tag) is immobilized on the surface of the magnetic microparticle via the capture molecule. Although such other molecule, namely, a capture tag or a capture molecule, is not limited, it may, for example, be a nucleic acid molecule (such as an RNA molecule) or a protein molecule (such as an antibody), and can be bound to the biomolecule to be analyzed or the magnetic microparticle by any method known in the art (such as a ligation reaction using a ligase, a coupling reaction using a functional group, a bond via a binding molecule, or a reaction using a bond between biotin and avidin or streptavidin).

The immobilization of a biomolecule onto a magnetic microparticle using a covalent bond can be performed by, for example, introducing a functional group into the biomolecule to be analyzed or a capture tag, introducing a functional group reactive with the former functional group into the surface of a magnetic microparticle or a capture molecule, and causing a reaction between these functional groups. A covalent bond can be formed by introducing, for example, an amino group into a biomolecule or a capture tag and introducing an active ester group, an epoxy group, an aldehyde group, a carbodiimide group, an isothiocyanate group or an isocyanate group into a magnetic microparticle or a capture molecule. Alternatively, a mercapto group may be introduced into a biomolecule to be analyzed or a capture tag with an active ester group, a maleimide group or a disulfide group introduced into a magnetic microparticle or a capture molecule. As one method for introducing a function group into the surface of a magnetic microparticle, the magnetic microparticle is treated with a silane coupling agent having a desired functional group (such as γ-aminopropyl triethoxy silane). Another method for introducing the functional group which functions as the binding site into the magnetic microparticle may be plasma treatment. Further, as a method for immobilizing a biomolecule or a capture tag onto a magnetic microparticle by the physical adsorption, charge of the biomolecule or the capture tag may be used for electrostatically binding it to a magnetic microparticle having been subjected to a surface treatment with a polycation (such as polylysine, polyallylamine or polyethyleneimine).

It is preferred that each of the biomolecules to be analyzed is immobilized on each microparticle. Each biomolecule can be immobilized by, for example, binding one capture molecule to a magnetic microparticle and immobilizing the biomolecule to be analyzed on the magnetic microparticle via the capture molecule. The magnetic microparticle is preferably surface coated so as to prevent another substance (such as a nucleic acid or a protein) from being adsorbed thereon.

The magnetic microparticles are preferably dispersed in a suitable solution. Specifically, the method of the present invention may include a step of dispersing the magnetic microparticles in a solution. The solution that can be used is any solution as long as it does not inhibit the immobilization of the biomolecules onto the magnetic microparticles, the reaction between the biomolecules and the probe molecules and the like. Examples of the solution include water, a saline buffer (such as physiological salt solution), a Tris buffer, alcohol (such as methanol or ethanol), ketone (such as acetone), and ether (such as diethyl ether or tetrahydrofuran), and a dispersing agent may be added thereto if necessary.

The support substrate on which the magnetic microparticles are collected and immobilized is not particularly limited as long as it is prepared from a material generally used in the art as a carrier or a support. Examples include a sheet, a membrane, a gel thin film, a capillary plate and a film. The support substrate is preferably in a planar shape considering the label measuring step performed subsequently. Examples of the material of the support substrate include a metal such as gold, silver, copper, aluminum, tungsten, molybdenum, chromium, platinum, titanium or nickel; an alloy such as stainless steel, hastelloy, Inconel, Monel or duralumin; a glass material such as glass, quartz glass, fused quartz, synthetic quartz, alumina, sapphire, ceramics, forsterite or photosensitive glass; a plastic such as a polyester resin, polystyrene, a polyethylene resin, a polypropylene resin, an ABS (Acrylonitrile Butadiene Styrene) resin, nylon, an acrylic resin, a fluororesin, a polycarbonate resin, a polyurethane resin, a methyl pentene resin, a phenol resin, a melamine resin, an epoxy resin or a vinyl chloride resin; and agarose, dextran, cellulose, polyvinyl alcohol, nitrocellulose, chitin and chitosan.

The collection and immobilization of the magnetic microparticles on the support substrate can be performed by using magnetic force, for example, by using a magnet. The magnetic microparticles are collected and immobilized on the support substrate preferably in a single layer for performing the label measuring step described hereinbelow.

Immobilization of the biomolecules or the microparticles on the support substrate can be performed in the same manner as the immobilization of the biomolecules on the microparticles described above. Further, the microparticles can be immobilized on the support substrate via adhesive pads. Specifically, an adhesive pad is formed in an immobilization position for the microparticle on the support substrate, and the microparticle is immobilized on the support substrate by binding the microparticle to the adhesive pad.

The adhesive pad is not particularly limited as long as it is made of a material different from the support substrate. Examples of the material include a metal such as gold, titanium, nickel or aluminum, and a metal oxide. A method for providing the adhesive pad on the support substrate is not also particularly limited, and the adhesive pad may be formed, for example, by a thin film forming process utilized in the field of semiconductors, specifically, by deposition and sputtering, or by dry or wet etching performed after deposition and sputtering. Immobilization of the biomolecules or the microparticles on the adhesive pads is also performed in the same manner as the immobilization of the biomolecules on the microparticles described above.

The individual biomolecules to be analyzed are preferably immobilized, one molecule per position, in positions spatially separated from one another. Therefore, the adhesive pads are preferably formed on the support substrate with regularity. In particular, the distance between and the positions of the adhesive pads are determined so that the respective microparticles (namely, the respective biomolecules) can be immobilized in positions spatially separated from one another. The number of microparticles (namely, biomolecules) to be immobilized on each adhesive pad is preferably one. In order to perform such immobilization, the concentration of the biomolecules to be analyzed or the microparticles is adjusted, so that the number of biomolecules can be smaller than the number of immobilization positions or adhesive pads provided on the support substrate. Further, by bringing the biomolecules to be analyzed or the microparticles into contact with the support substrate by stirring the solution containing them, collision frequency can be increased so as to increase the immobilization ratio.

Subsequently, the label is measured on the support substrate, and the measurement of the label can be performed by using any of methods and devices known in the art in accordance with the type of the label. For example, a fluorescent label, a luminescent semiconductor label or a chemiluminescent label can be measured by using an optical system for exciting the label with suitable laser light and counting emitted light, a fluorescent microscope, a plate reader or the like. Alternatively, if an enzyme label is used, the label can be measured by adding a matrix that is decomposed through an enzyme function to develop a color and optically measuring the amount of decomposed matrix. If a radioactive label is used, the radiation dose emitted by the radioactive label is measured by a scintillation counter or the like. In the method of the present invention, biomolecules are preferably quantitatively analyzed by using fluorescence and by counting obtained fluorescent light spots. For example, a common label added to the biomolecules to be analyzed and a different label added to the probe molecules are measured, and the ratio therebetween is calculated, and thus, the quantity of reacted biomolecules in the total quantity of the biomolecules to be analyzed can be evaluated.

As described above, the presence and/or the quantity of biomolecules of interest in the biomolecules to be analyzed can be analyzed. After the analysis, the biomolecules to be analyzed having been immobilized on the magnetic microparticles can be used for a reaction with different probe molecules by removing the probe molecules from the biomolecules to be analyzed, or the magnetic microparticles can be used for an analysis reaction of different biomolecules by removing the biomolecules to be analyzed having been immobilized thereon. Such removal of molecules is performed by a method depending upon the reaction and means used in the immobilization and the binding of the molecules, and can be performed by, for example, heat denaturation (a high temperature treatment).

The present invention also relates to an apparatus for practicing the aforementioned method for analyzing biomolecules of the present invention. A biomolecule analyzer of the present invention includes, for example, the following:

means for immobilizing biomolecules to be analyzed onto magnetic microparticles;

means for reacting the labeled probe molecules and the biomolecules to be analyzed;

means for collecting and immobilizing the magnetic microparticles on a support substrate after the reaction; and means for measuring a label.

The means for immobilizing the biomolecules on the magnetic microparticles includes, for example, means for supplying the biomolecules to be analyzed, means for supplying the magnetic microparticles, and a reaction chamber for mixing the biomolecules to be analyzed and the magnetic microparticles.

The means for reacting the biomolecules to be analyzed and the magnetic microparticles includes, for example, a material on which biomolecules or capture molecules are immobilized (also designated as a "biomolecule analysis device"), means for supplying the probe molecules, a reaction chamber for mixing the biomolecules to be analyzed and the probe molecules, and temperature controlling means.

The means for collecting and immobilizing the magnetic microparticles on a support substrate includes, for example, a magnet unit and a washing unit.

The means for measuring a label includes, for example, light irradiating means and emission detecting means if a fluorescent label, a luminescent semiconductor label or a chemiluminescent label is measured. The light irradiating means and the emission detecting means can be selected and designed in accordance with the types and excitation and emission wavelengths and the like of label to be used.

The biomolecule analyzer of the present invention can further include means for supplying a washing (cleaning) solution, means for draining the washing solution, means for recording analysis results, means for comparing the analysis results with database, and the like.

EXAMPLES

The aforementioned and other novel features and effects of the present invention will now be described with reference to the accompanying drawings. A specific embodiment will be described here in detail so as to make the present invention completely understood. However, it is noted that the present invention is not limited to the following description.

Example 1

An analysis method of this example will be described by taking, as an example, a case where the biomolecules to be analyzed are nucleic acids with reference to FIG. 1. Capture tag 102 labeled with fluorescent dye 103 is bound to each of the nucleic acid fragments 101 to be analyzed. For binding, it is possible to employ a ligation reaction, or a coupling reaction between functional groups wherein functional groups such as an amino group and a succinimide group are introduced in advance into nucleic acid fragment 101 to be analyzed and capture tag 102 and these may be coupled. In particular, if the nucleic acid fragments 101 to be analyzed are micro RNAs, then a binding method in which an RNA molecule with a length of about 10 to 20 bases is used as the capture tag 102 and a T4 RNA ligase is used for binding them is effective. After binding capture tag 102 labeled with fluorescent dye 103 to each of the nucleic acid fragments 101 to be analyzed, the resultant is hybridized with nucleic acid molecules (probe molecules) 104 each labeled with fluorophore 105. Nucleic acid molecule 104 is used for identifying each of the nucleic acid fragments, and is necessary to have a nucleotide sequence representative of each of the gene sequences. When designing sequences, it is necessary that individual labeled nucleic acid molecules have a melting temperature, which serves as a stability index of a nucleic acid double strand, falling in a prescribed range. The range is preferably smaller, and is preferably suppressed to approximately ±3° C. of a prescribed temperature. Further, homology in the nucleotide sequence among the labeled nucleic acid molecules is preferably lower, and the homology is suppressed preferably to 70% or less, and more preferably to 60% or less. Then, a method described in Example 6 is employed to prepare in advance magnetic microparticles 108 on each of which merely one capture molecule 106 is immobilized via a binding molecule 107. The hybridization is performed by adding the magnetic microparticles, resulting in preparing the magnetic microparticles 108 on each of which a molecular pair of a hybrid of the nucleic acid fragment 101 to be analyzed and the nucleic acid molecule 104 labeled with the fluorophore 105 is formed. As fluorophore 105, a general fluorescent dye molecule of Cy3 or Cy5, a semiconductor microparticle of Zn—Se or the like, or a dendrimer having several hundred molecules of a fluorescent dye adhered thereto commercially available from Genisphere, Inc. can be used.

Next, magnetic microparticles 108 on which the hybrids have been formed are collected and immobilized on a support substrate 110 by using a magnet 109.

Finally, fluorescence of fluorescent dye 103 and fluorophores 105 is measured with detector 111, so as to calculate the numbers of fluorescent light spots of fluorescent dye 103 and each type of fluorophore 105. The number of fluorescent light spots of fluorescent dye 103 corresponds to the total number of nucleic acid fragments 101 to be analyzed, and the number of fluorescent light spots of each type of fluorophores 105 corresponds to the number of each corresponding type of nucleic acid fragment. Accordingly, by calculating the ratio therebetween, the ratio of the number of each type of the nucleic acid fragments to the total number of nucleic acid fragments to be analyzed can be calculated. The ratio thus calculated is particularly useful for comparative expression analysis of nucleic acid fragments between samples. For example, when searching for a marker gene having a different expression level between a healthy person and a patient having a specific disease, it is necessary to find a gene having an equivalent expression level in both samples to normalize the expression level. However, in actuality it is extremely difficult to find a gene having an equivalent expression level in the samples. This difficulty is specifically reported when employing quantitative PCR (Nature Methods 2010, Vol. 7, pp. 687-692). By contrast, in the method of this example, the ratio of each type of biomolecule in the whole sample can readily be calculated, and therefore, it is possible to directly compare a healthy person and a patient by comparing the ratios of each type of biomolecule to the whole biomolecules (entirety of biomolecules) in the samples. This is particularly useful for comparative analysis of nucleic acid molecules in a clinical specimen.

If there are many kinds of biomolecules to be identified, fluorescent beads containing fluorophores can be used as fluorophores 105 used for labeling. For example, when two types of fluorophores are used in contents of ten levels each and the two types of fluorophores are mixed in various levels of the contents, 100 types of fluorescent beads can be prepared. If three types of fluorophores are used, a bead set usable for identifying 1000 types can readily be prepared. A fluorescent bead set usable for identifying 100 types through excitation with laser lights of two wavelengths is commercially available from Luminex Trading Inc. The fluorescent beads are chemically modified in their surfaces and bound to nucleic acid molecules, and thus, fluorophore-labeled nucleic acid molecules 104 can be prepared. After hybridization, non-specific adsorbates are appropriately removed by washing, and then, nucleic acid fragments 101 to be analyzed are analyzed by detecting fluorescence. If fluorophore-labeled nucleic acid molecules (probe molecules) 104 use, as the fluorescent label, merely one molecule of a general fluorescent dye such as Cy3 or Cy5, then single molecule fluorescence is observed in a portion on support substrate 110 where each of the nucleic acid fragments 101 to be analyzed is immobilized. In this case, since the fluorescence is weak, a highly sensitive fluorescence detector such as an electron multiplying CCD (EM-CCD) is necessary. If fluorescent beads are used as the fluorophore, fluorescence with intensity higher than one molecule fluorescence is emitted, and hence, a general CCD can be sufficiently used for the detection.

When single-molecule immobilized magnetic microparticles 108 (in number of $10^8$) and the nucleic acid molecules 104 (in 1.7 nM) were reacted in a fluid volume of 10 ul under stirring, the reaction efficiency reached a saturation value during a reaction time of approximately 3 hours. This time period is much shorter than the time period (14 to 16 hours) necessary for general hybridization performed in a DNA microarray described in "A molecular Cloning Manual DNA Microarrays 2002, Cold Spring Harbor Laboratory Press, pp. 228-239", and it was thus revealed that the binding reaction can proceed rapidly. Accordingly, it can be stated that the binding reaction between a biomolecule and a nucleic acid molecule used as a probe molecule can be carried out rapidly and the biomolecule analysis can be performed rapidly in the present invention.

In the example described above, each biomolecule of the sample to be analyzed is immobilized on one microparticle. While counting can readily be performed by fixing one biomolecule per microparticle, this is not a prerequisite of the present invention. So long as counting can be performed, two or three biomolecules may be immobilized on one microparticle, and in such case, the object of the present invention to analyze the type and the abundance of a biomolecule sample to be analyzed can be achieved as well.

Example 2

Figure 2:
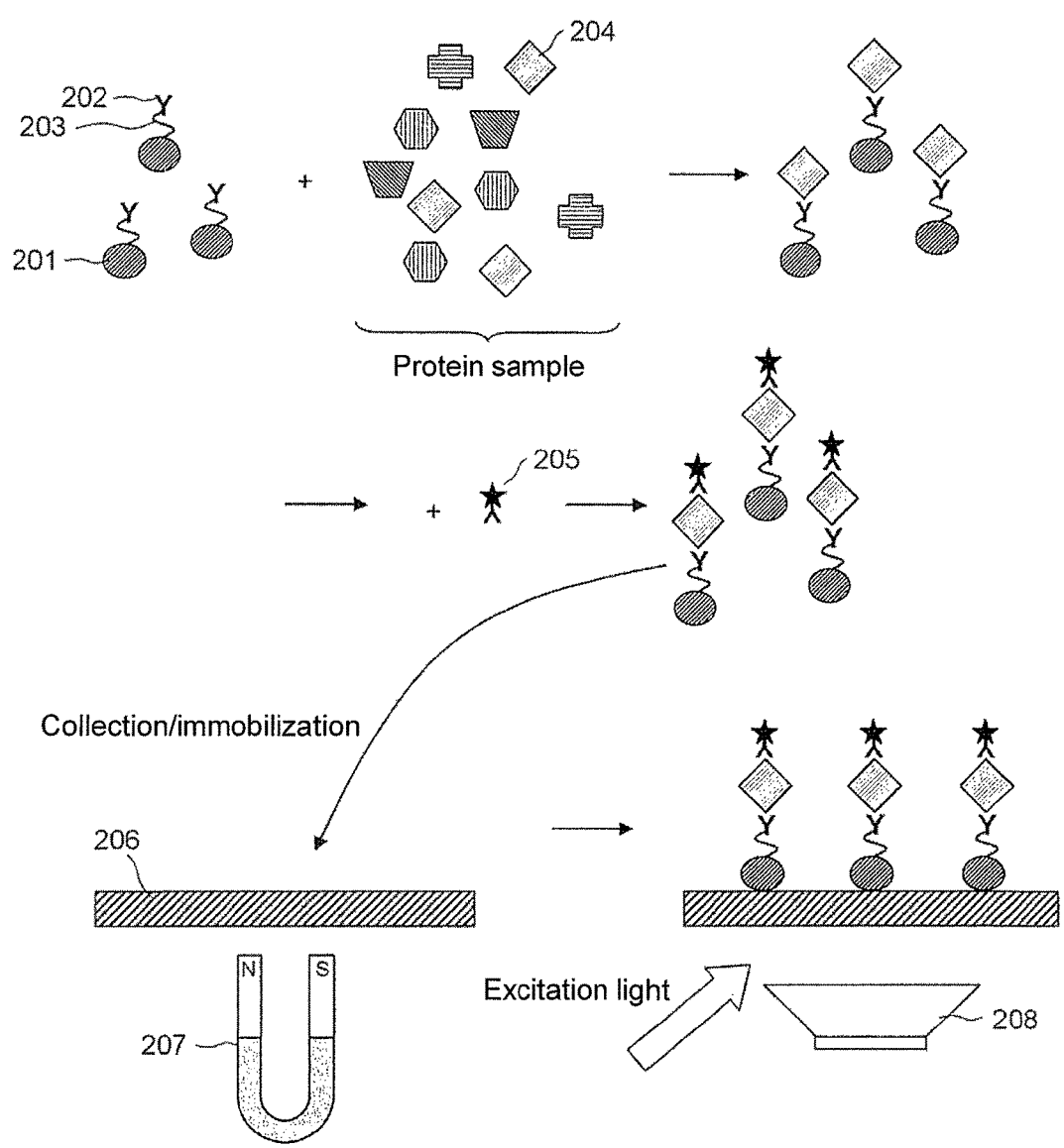
FIG. 2 is a diagram illustrating an exemplified analysis method of another example.

An analysis method of this example will be described by taking, as an example, a case where the biomolecules to be analyzed are protein with reference to FIG. 2.

Antibody 202 specifically binding to protein 204 to be analyzed is immobilized on the surface of each magnetic microparticle 201 via a binding molecule 203. Magnetic microparticles 201 are not particularly limited, but preferably have high dispersibility because it is necessary for the same to react with a protein sample in a solution. The diameter of said microparticles is preferably 100 μm or less, and more preferably 10 μm or less. When the antibody-bound microparticle is reacted with the protein sample in a solution, the protein 204 to be analyzed is captured on the magnetic microparticle 201. Then, this resultant is reacted with antibody (probe molecule) 205 labeled with a fluorescent dye, and thus, protein 204 to be analyzed having been captured on magnetic microparticle 201 can be fluorescence labeled. Thereafter, magnetic microparticles 201 can readily be collected and immobilized on the surface of support substrate 206 by using magnet 207. Next, protein 204 to be analyzed having been collected on the surface of support substrate 206 is irradiated with light, and fluorescent light spots are detected by detector 208. Since the number of fluorescent light spots is correlated with the concentration of protein 204 to be analyzed, information about the concentration of protein 204 to be analyzed can be obtained by obtaining the number of light spots. In particular, by using the method described in Example 6, microparticles wherein merely one molecule of antibody 202 is immobilized on each magnetic microparticle 201 can be prepared in advance. Then, by using the same, it is possible to determine the absolute concentration of protein 204 being analyzed.

Example 3

Figure 3:
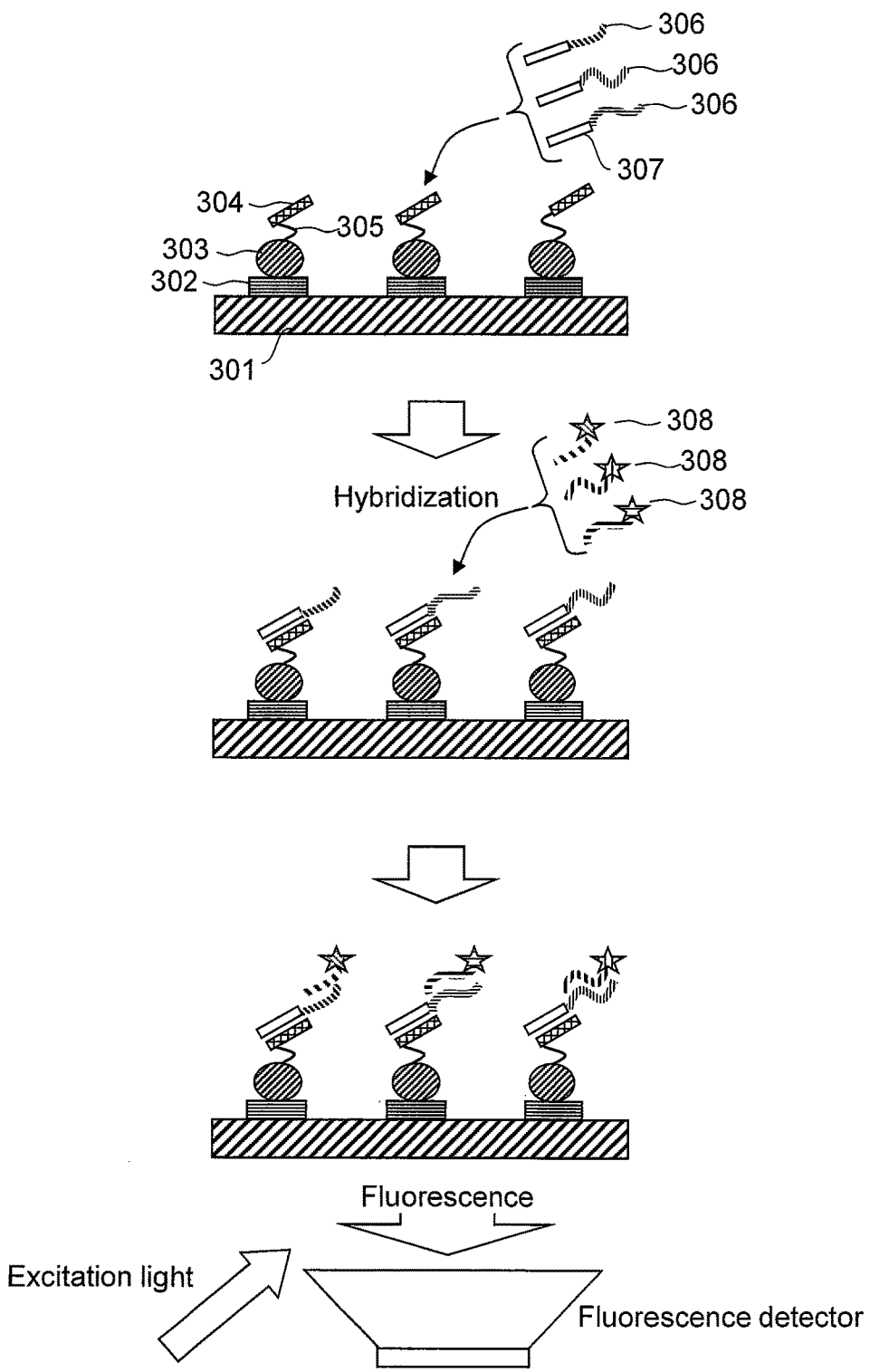
FIG. 3 is a diagram illustrating an exemplified analysis method of another example.

A device configuration and an analysis method of this example will be described with reference to FIG. 3.

The device configuration of this example is as follows. Adhesive pads 302 are formed on support substrate 301. As support substrate 301, a glass substrate of quartz or the like, a silicon wafer or the like can be used. Adhesive pads 302 can be made of any material different from support substrate 301, and are made of a metal or a metal oxide. A method for forming adhesive pads 302 will be described in detail in Example 5. Adhesive pads 302 are formed on support substrate 301 preferably with regularity, which will be described in detail in Example 5. Microparticles 303 are immobilized on the adhesive pads 302. The number of microparticles immobilized per each adhesive pad is one. On each microparticle 303, merely one capture molecule 304 is immobilized via binding molecule 305. Depending upon the type of nucleic acid fragments 306 to be analyzed, various combinations of molecule groups can be used as capture tag molecule 307, capture molecule 304 and binding molecule 305. If, for example, nucleic acid fragment 306 to be analyzed is a reverse transcribed product of RNA, then the capture tag molecule 307 can be a primer DNA used in the reverse transcription, and capture molecule 304 can be a nucleic acid molecule having a complementary sequence to capture tag molecule 307. Alternatively, capture tag molecule 307 can be a nucleic acid molecule having biotin at the end, and capture molecule 304 can be a molecule having avidin at the end. Binding molecule 305 can be an alkane molecule having about 10 or less carbon atoms, or a molecule binding to capture molecule 304 through a chemical bond and having biotin at the other end. In this case, the surface of microparticle 303 is preferably modified with avidin, streptavidin or the like. The reaction between capture tag molecule 307 and capture molecule 304 is preferably hybridization reaction if these molecules are nucleic acid molecules having complementary sequences. Alternatively, it is also preferable to bind them through a chemical bond by ligation. As a result, on support substrate 301, individual nucleic acid fragments 306 to be analyzed are immobilized respectively to be isolated from one another in a regular arrangement. In order to obtain the absolute number of the nucleic acid fragments 306 to be analyzed, the numbers of adhesive pads 302 and microparticles 303 are set to be larger than the number of nucleic acid fragments 306. The total number of molecules of nucleic acid fragments 306 can be estimated based on the total weight of nucleic acid fragments 306. The total weight is obtained based on the absorbance at a wavelength of 260 nm. A sample is diluted into such a concentration that the number of molecules thus calculated can be smaller than the number of adhesive pads 302. The following method is employed in order to immobilize a larger number of nucleic acid fragments 306 to be analyzed. For example, the surfaces of adhesive pads 302 are covered by alkane molecules as binding molecules, so as to bind, by intermolecular force, to microparticles 303 composed of a polymer such as polystyrene. In this manner, the binding can be rapidly caused merely by bringing microparticles 303 close to the adhesive pads 302, and once adhered, the microparticles never peel off. Further, the immobilization ratio can be increased by increasing the frequency of collision of microparticles 303 against adhesive pads 302. In order to increase the collision frequency, a solution containing microparticles 303 is preferably stirred. Specifically, a groove or a projection is provided in a channel where the solution containing microparticles 303 passes, so as to change the flow from a laminar flow to a turbulent flow. Here, the thickness of the solution on support substrate 301 where adhesive pads 302 are disposed is preferably smaller, thereby increasing the collision frequency. This channel configuration will be described in detail in Example 9. In order to confirm that all microparticles 303 have been bound to adhesive pads 302, the reacted solution is dried out and fixed on the substrate, and then, it may be confirmed that no capture tag molecule 307 can be detected through binding by the ligation.

Next, the types of nucleic acid fragments 306 to be analyzed thus immobilized are identified and the abundances are obtained. Fluorophore-labeled nucleic acid molecules (probe molecules) 308 are reacted with support substrate 301 on which nucleic acid fragments 306 to be analyzed are immobilized. Fluorophore-labeled nucleic acid molecules (probe molecules) 308 include nucleic acid sequences complementary to those of the nucleic acid fragments 306 to be analyzed. For the fluorophore labeling, a general fluorescent dye molecule such as Cy3 or Cy5 or semiconductor microparticles of Zn—Se or the like can be used. If there are many types of nucleic acid fragments to be evaluated to be identified, fluorescent beads containing fluorophores can be used for the fluorophore labeling. For example, when two types of fluorophores are used in contents of ten levels each and the two types of fluorophores are mixed in various levels of contents, 100 types of fluorescent beads can be prepared. If three types of fluorophores are used, a bead set usable for identifying 1000 types can readily be prepared. For example, a fluorescent bead set usable for identifying 100 types through excitation with laser lights of two wavelengths is commercially available from Luminex Trading Inc. The surfaces of these fluorescent beads are chemically modified and bound to nucleic acid molecules, and thus, fluorophore-labeled nucleic acid molecules (probe molecules) 308 can be prepared.

After hybridization, non-specific adsorbates are appropriately removed by washing, and then, nucleic acid fragments 306 to be analyzed are analyzed by detecting fluorescence. If fluorophore-labeled nucleic acid molecule (probe molecule) 308 uses, as the fluorescent label, merely one molecule of a general fluorescent dye such as Cy3 or Cy5, single molecule fluorescence is observed in a portion on support substrate 301 where the nucleic acid fragment 306 to be analyzed is immobilized. In this case, since the fluorescence is weak, a highly sensitive fluorescence detector such as an EM-CCD is necessary. If fluorescent beads are used as the fluorophore, fluorescence with intensity higher than one molecule fluorescence is emitted, and hence, a general CCD can be sufficiently used for the detection. Adhesive pads 302 are formed on support substrate 301 with regularity, for example, in a lattice shape, and therefore, fluorescent light spots are observed in positions with regularity also in a fluorescent image. Accordingly, even if a fluorophore-labeled nucleic acid molecule (probe molecule) 308 is non-specifically adhered onto support substrate 301, such molecule can readily be recognized and removed from the positions of the light spots in a fluorescent image. This is practically a very useful feature in analysis of a trace sample and in observation of weak fluorescence. For identifying fluorophores or fluorescent beads, an emission spectrum is diffracted by using a diffraction grating to irradiate the photosensitive surface of a CCD, and each type of the fluorophores or fluorescent beads can be identified by examining the intensity of each pixel divided in a wavelength direction. Alternatively, each type of the fluorophores or fluorescent beads may be identified by using the ratio between reflected light and transmitted light obtained by using a dichroic mirror provided with reflection characteristics largely depending upon the wavelength. After identifying each of the light spots, resulting data is compiled, so that the types of nucleic acid fragments 306 to be analyzed and the numbers of light spots, namely, information about the abundance (the absolute concentration), can be ultimately obtained. For example, if adhesive pads 302 are formed at a pitch of 1 μm, there are $10^6$ adhesive pads in a 1 mm square, and therefore, it can be checked how many molecules of a specific type of nucleic acid fragments of interest are present among a maximum total number of $10^6$ molecules.

The present method will now be described in more detail by taking micro RNAs as an example of a specific analysis object.

If micro RNAs are to be analyzed, sequence data of respective micro RNA molecules can be obtained from known nucleotide sequence databases of micro RNAs (available from, for example, http://www.microrna.org). Based on the data thus obtained, a primer for reverse transcription can be designed. The length of the primer is preferably about 10 to 15 bases, and a 10-base DNA is added at the 5'-end as the capture tag molecule 307. With respect, for example, to human micro RNAs, 1000 types of primers are designed and synthesized. The thus synthesized 1000 types of primers are mixed in equivalent amounts to prepare a primer cocktail. With respect to total RNAs, the cocktail of reverse transcription primers and a reverse transcriptase are mixed, and then, a reverse transcription reaction is caused under an environment of 37 to 40° C. to synthesize cDNAs. Thus, nucleic acid fragments 306 to be analyzed and capture tag molecules 307 are bound to each other. Alternatively, RNAs are used as the nucleic acid fragments 306 to be analyzed and RNAs of about 10 bases are used as capture tag molecules 307, and they are bound to be each other by using a T4RNA ligase. Thus, nucleic acid fragments 306 to be analyzed can be bound to capture tag molecules 307. On each of the microparticles 303, one molecule of a complementary strand DNA to the 10-base nucleic acid used as capture tag molecule 307 is immobilized in advance as capture molecule 304. The immobilization of one molecule of capture molecule 304 on microparticle 303 will be described in detail in Example 8. The cDNAs (i.e., the nucleic acid fragments 306 to be analyzed bound to capture tag molecules 307) are hybridized on the support substrate by a conventional method, and thus, nucleic acid fragments 306 to be analyzed are immobilized on the support substrate.

In the same manner as described above, sequence data of respective micro RNA molecules are obtained from the known nucleotide sequence database of micro RNAs, and nucleotide sequences thus found in the database are modified with biotin at the 5'-end, so as to synthesize 1000 types of synthetic oligos.

The fluorophores used in the fluorescent beads can be, for example, Cy5, Cy5.5 and Cy3, and two wavelengths of 532 nm and 633 nm can be employed as the excitation light. With solutions containing the respective dyes in different concentration ratios prepared, each solution is mixed with beads at a stage where the polystyrene beads are synthesized from a styrene monomer, so that polystyrene beads having a prescribed dye mixing ratio can be prepared. In order to modify the surface of the polystyrene with avidin or the like, a carboxyl group is introduced in advance to the bead surface by using a copolymerization reaction between acrylic acid/methacrylic acid and styrene, and an amino group of avidin is reacted with carbodiimide used as a crosslinking agent, and thus, the bead surface can readily be modified.

Fluorophore-labeled nucleic acid molecules (probe molecules) 308 can be synthesized by reacting avidin modified fluorescent beads and synthetic oligonucleotides having biotin modified 5'-ends.

Next, fluorophore-labeled nucleic acid molecules (probe molecules) 308 are hybridized by a general method on support substrate 301 on which nucleic acid fragments 306 to be analyzed have been immobilized.

After washing the resulting substrate with a washing solution containing sodium dodecyl sulfate, a fluorescent image is obtained. After recognizing which types of fluorescent beads the fluorescent light spots of the respective adhesive pads 302 correspond to, the light spots are counted, and thus, the abundances of various types of micro RNAs can be analyzed.

The number of types of nucleic acids that can be detected depends upon the number of types of fluorescent beads that can be identified. Assuming that there are approximately 1000 types of micro RNAs, 1000 types of fluorescent beads may be prepared. As described above, with each fluorophore used in a content at any of ten levels, three types of fluorophores are mixed respectively in different levels of contents, so that a bead set usable for identifying 1000 types can readily be prepared, and thus, the whole types of the micro RNAs can be detected at one time. Alternatively, if the expression level of a specific type of micro RNAs alone is desired to find, fluorophore-labeled nucleic acid molecules (probe molecules) 308 corresponding to the specific type of micro RNAs are prepared, and fluorescent beads are prepared in a corresponding number. With respect to micro RNAs of types other than the specific type of micro RNAs, the same fluorescent beads can be commonly used. In this manner, without preparing 1000 types of fluorescent beads, the abundance of the whole micro RNAs can be found as the counted number of light spots. Further, an abundance ratio of the specific type of micro RNAs to the whole micro RNAs can be obtained.

Alternatively, capture tag molecules 307 may be labeled in advance with a common fluorescent dye that has a different emission wavelength or emission intensity from fluorophore-labeled nucleic acid molecules 308, so that the number of fluorescent light spots caused by the fluorescent dyes labeling the capture tag molecules 307 can be regarded to correspond to the total number of nucleic acid molecules of the sample, and that the number of fluorescent light spots caused by each fluorophore labeling the fluorophore-labeled nucleic acid molecules (probe molecules) 308 can be regarded to correspond to the number of a corresponding type of nucleic acid molecules of the sample. Thus, the ratio among these light spots can be determined as an abundance ratio among the respective types of nucleic acid molecules of the sample, and this is extremely effective if the expression level of a specific type of nucleic acid molecules alone is needed.

Moreover, the method of the present invention is applicable not only to the analysis of a nucleic acid sample but also to the analysis of biomolecules other than the nucleic acid samples, such as proteins, by optimizing capture molecules 304. If a biomolecule sample contains multiple types of biomolecules, each of biomolecules 306 to be analyzed is immobilized in each of positions with regularity on support substrate 301 by using a suitable antibody or the like as capture molecule 304. Probe molecules 308 known to bind to a specific biomolecule are reacted with biomolecules 306 having been immobilized on support substrate 301, and probe molecules 308 are detected, so as to analyze the biomolecules in the same manner as in the case of the nucleic acid sample. Accordingly, the type and the absolute number of biomolecules to be analyzed can be evaluated, and the biomolecules can be simply and rapidly analyzed with single molecule sensitivity and resolution.

Example 4

Figure 4:
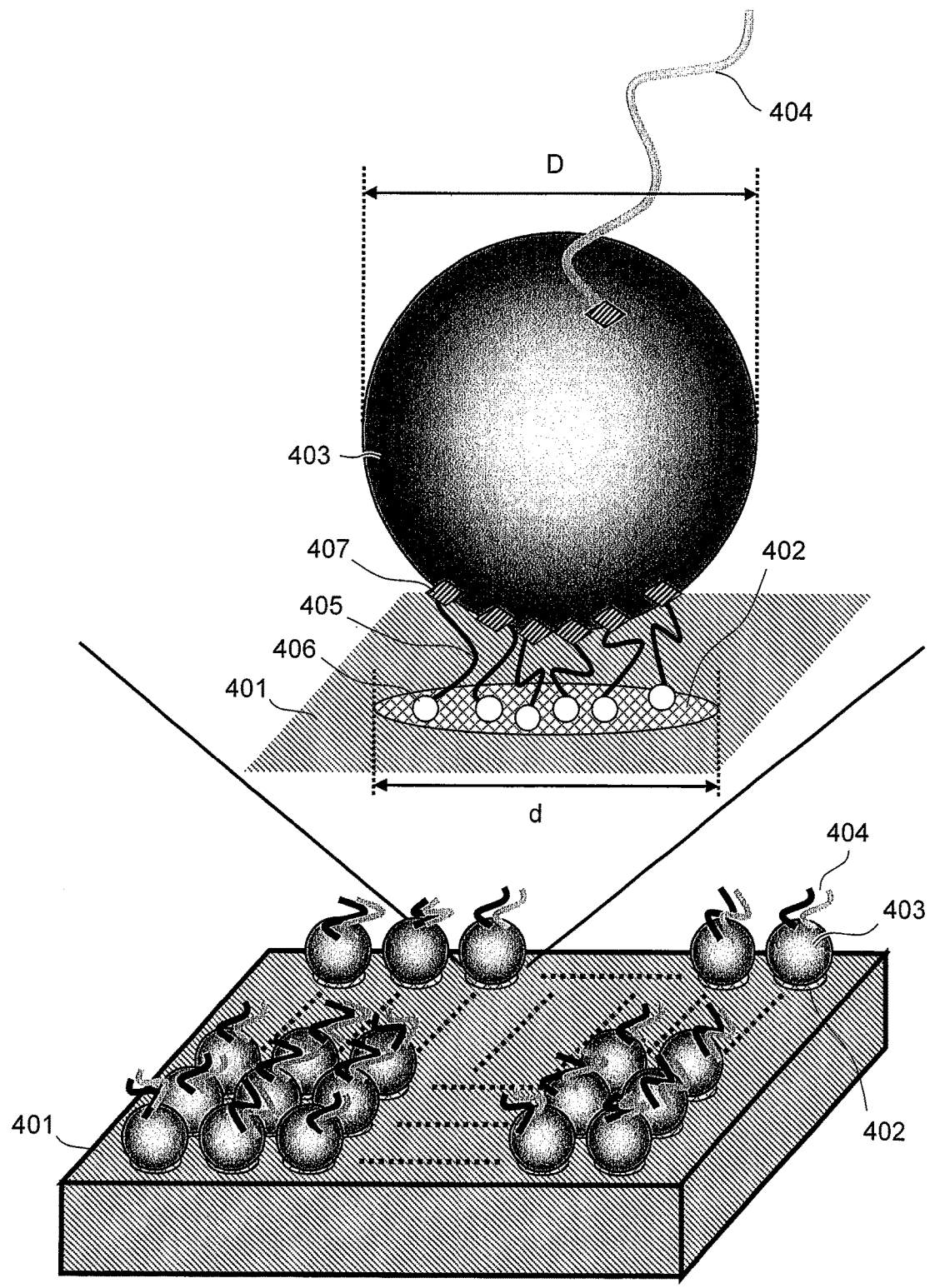
FIG. 4 is a diagram illustrating an exemplified configuration of a device used in an analysis method of one example.

A device configuration of this example will be described with reference to FIG. 4. On support substrate 401, adhesive pads 402 are formed with regularity, for example, in a lattice shape as illustrated in FIG. 4. Each adhesive pad 402 and microparticle 403 are linked with each other via linear molecules 405 by a chemical bond or chemical interaction. Functional group 406 at the end of each linear molecule 405 is bound to adhesive pad 402 preferably by the chemical interaction. At this point, functional group 406 preferably has weak interaction with support substrate 401 and strong interaction with adhesive pad 402. From such perspective, support substrate 401 can be quartz glass, sapphire or a silicon substrate. Further, adhesive pads 402 can be made of a material selected from gold, titanium, nickel and aluminum. It is necessary to select the functional group 406 by considering the combination with support substrate 401 and adhesive pad 402, and for example, a sulfhydryl group, an amino group, a carboxyl group, a phosphate group, or an aldehyde group can be used as functional group 406. Linear molecules 405 serve to link microparticle 403 to adhesive pad 402 and are not largely limited in their length, but if linear molecules 405 have a low molecular weight, a straight chain molecule having about 3 to 20 carbon atoms is preferably used. Another functional group 407 at the other end of linear molecule 405 provides adhesion to microparticle 403. If a polymer is used as linear molecules 405, then a polymer having a plurality of side chains, including a side chain having functional group 406 and a side chain having functional group 407, can be used. As microparticles 403, metal microparticles or semiconductor microparticles can be used. For example, gold microparticles having a diameter of 5 nm to 100 nm are commercially available to be used in the present invention. Alternatively, semiconductor microparticles of a compound semiconductor such as CdSe having a diameter of about 10 nm to 20 nm are commercially available to be used in the present invention. The functional group usable as functional group 407 depends on the type of microparticles, and for example, if gold microparticles are used, functional group 407 is preferably a sulfhydryl group, an amino group or the like. If semiconductor microparticles are used, microparticles having surfaces modified with streptavidin are commercially available, and biotin can be used as functional group 407. Alternatively, microparticles of a polymer material such as polystyrene can be used as microparticles 403. If a polymer material is used, the particle size of the microparticles can be made uniform, and the particle size can be selected from a wide range of several tens of nm to several μm. Further, a functional group of a polymer material is preferably used as scaffold for surface modification, and thus, the amount of functional groups introduced for immobilization of capture molecules 404 to be immobilized on the surfaces of the microparticles can be made uniform. In particular, merely one capture molecule 404 is preferably immobilized on the surface of each microparticle because the reproducibility of the immobilization ratio can be thus made very high.

As the capture molecule 404, a single strand of a nucleic acid molecule of a DNA or RNA can be used. An end of the nucleic acid molecule is modified in advance similarly to functional group 407 and reacted with microparticle 403. It is preferable that merely one capture molecule 404 is immobilized on each microparticle 403, and thus, merely one capture molecule 404 is immobilized on each adhesive pad 402.

If probes are identified by simple fluorescence detection, the probes are preferably away from one another by approximately 1 μm in consideration of diffraction limit. Accordingly, microparticle 403 suitably has a size of 1 μm or less.

As a method for forming adhesive pads 402 on support substrate 401, the thin film forming process already practically employed for semiconductors can be utilized. For example, a thin film is formed by deposition/sputtering through a mask or by deposition/sputtering, and then the thin film is dry or wet etched for forming the adhesive pads. Regular arrangement of the adhesive pads can readily be realized by employing the thin film forming process. A distance between the pads can be arbitrarily set, and if optical measurement is performed as detecting means, the distance therebetween is preferably 1 μm or more in consideration of the diffraction limit in the optical detection.

After forming adhesive pads 402 on support substrate 401, linear molecules 405 for linking microparticles 403 to adhesive pads 402 are supplied, so as to be immobilized on adhesive pads 402. Here, for purpose of preventing non-specific adsorption on support substrate 401, it is effective to react, on support substrate 401, a material having strong adhesion to support substrate 401 before supplying linear molecules 405. For example, a silane coupling agent or the like can be used. Next, microparticles 403 on which capture molecules 404 are immobilized are supplied onto support substrate 401, so as to be immobilized on adhesive pads 402, and thus, the biomolecule analysis device is completed.

When immobilizing microparticles 403 on adhesive pads 402, there is a possibility that a plurality of microparticles 403 may be immobilized on one adhesive pad 402. If a plurality of microparticles is immobilized, information of different types of biomolecules overlap, and hence, the analysis cannot be performed accurately. Therefore, it is necessary to immobilize one microparticle 403 on one adhesive pad 402. Accordingly, the present inventors made earnest studies by repeating immobilization experiments under various conditions, resulting in finding the following: If the condition that each adhesive pad 402 has a diameter d smaller than the diameter D of each microparticle 403 is met, then one microparticle 403 can be immobilized on one adhesive pad 402 (see, for example, WO 2010/087121). This is explained as follows: If microparticle 403 in a size equal to or larger than adhesive pad 402 is immobilized, then unreacted linear molecules are hidden by the immobilized microparticle(s) and hence cannot react with another microparticle. As a result of making further earnest studies, the following was found: If microparticle 403 has a charge on its surface, then electrostatic repulsion occurs between microparticles, and therefore, even if diameter d of each adhesive pad 402 is larger than diameter D of each microparticle 403, merely one microparticle is immobilized on each adhesive pad. In this manner, the following was revealed: If microparticle 403 has a small surface charge and shows weak electrostatic repulsion, then it is preferable that diameter d of each adhesive pad 402 be smaller than diameter D of each microparticle 403, and if microparticle 403 has large surface charge and shows strong electrostatic repulsion, then diameter d of each adhesive pad 402 need not necessarily be smaller than diameter D of each microparticle 403.

Example 5

Figure 5:
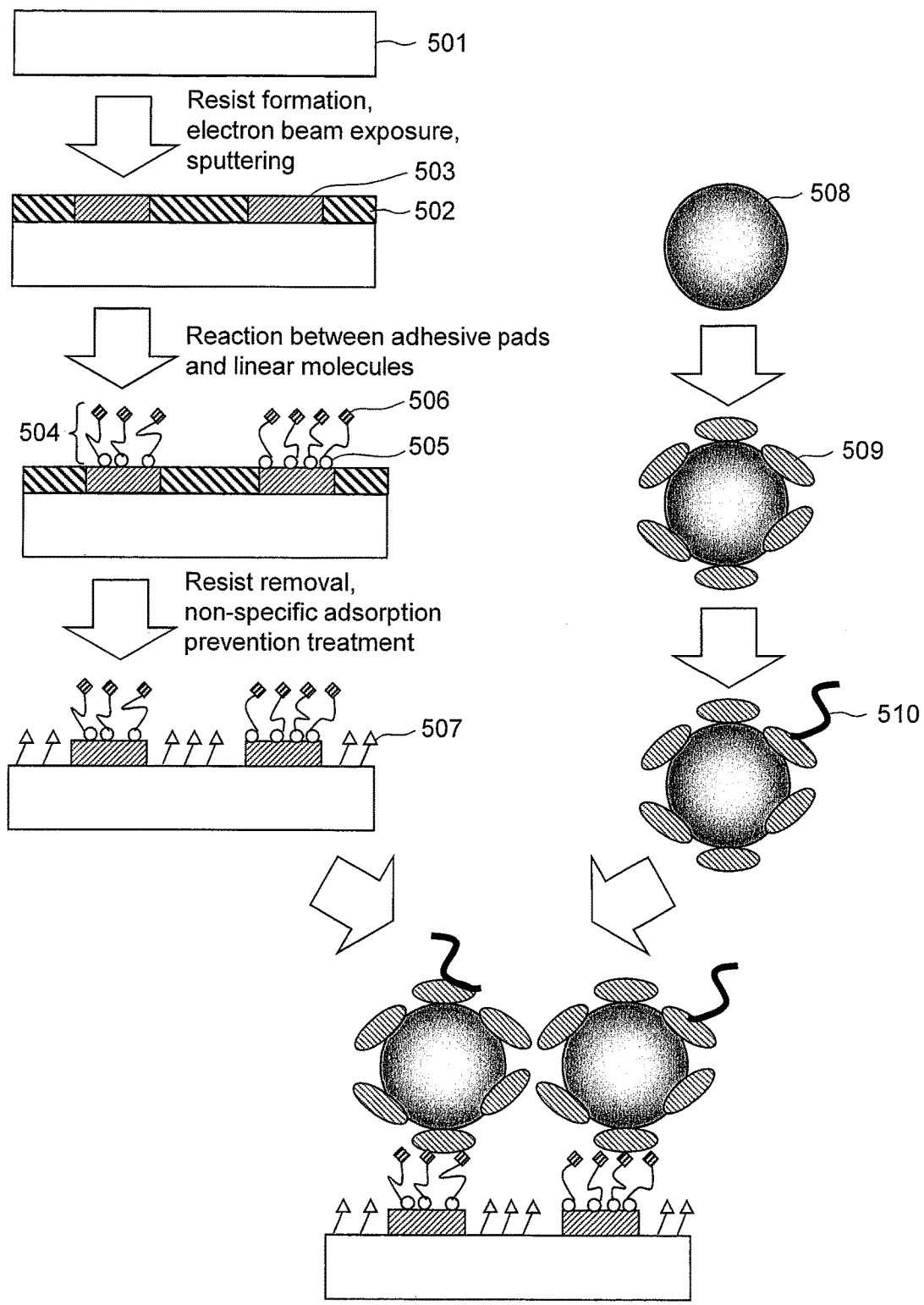
FIG. 5 is a diagram illustrating an exemplified method for producing a device used in an analysis method of one example.

A method for producing an analysis device of this example will be described with reference to FIG. 5. A smooth support substrate 501 is coated with an electron beam positive resist 502 by spin coating. As smooth support substrate 501, a glass substrate, a sapphire substrate, a silicon wafer or the like is used. If it is necessary, after produced into the device, to irradiate excitation light from a rear surface side opposite to a side where microparticles 506 are arranged, a quarts substrate or a sapphire substrate having excellent light transmission characteristics may be used. Examples of the electron beam positive resist 502 include polymethyl methacrylate and ZEP-520A (manufactured by Zeon Corporation, Japan). Through holes are formed in the resist by electron beam direct writing exposure after alignment performed by using positions of markers on support substrate 501. For example, through holes each having a diameter of 15 nm are formed. Although depending on the number of biomolecules that can be analyzed by parallel processing, the through holes are appropriately formed at a pitch of approximately 1 μm in consideration of simplicity in the production, high yield, and the number of biomolecules analyzable by parallel processing. The through-hole forming region also depends on the number of biomolecules analyzable by parallel processing, and in addition, largely depends on the position accuracy and the position resolution on the side of a detector. If, for example, reaction sites (adhesive pads) are formed at a pitch of 1 μm assuming that the through-hole forming region has a size of 1 mm×1 mm, a million reaction sites can be formed. After forming the through holes, a film is formed by sputtering a material of adhesive pads 503, such as gold, titanium, nickel or aluminum. If a glass substrate or a sapphire substrate is used as smooth support substrate 501 and, gold, aluminum or nickel is used as the material of adhesive pads 503, then a thin film of titanium or chromium is preferably formed between the material of the support substrate and the material of the adhesive pads for reinforcing adhesion therebetween. Next, linear molecules 504 are reacted with adhesive pads 503. If adhesive pads 503 are made of gold, titanium, aluminum or nickel, then functional group 505 at the end of each linear molecule 504 is preferably a sulfhydryl group, a phosphate group or a thiazole group, respectively. As a functional group 506 at the other end of linear molecule 504, for example, biotin can be used. After reacting linear molecules 504 with adhesive pads 503, the resist is removed. After removing the resist, a non-specific adsorption prevention treatment is performed on the surface of support substrate 501 in a portion where adhesive pads 503 are not formed. In order to prevent adsorption to fluorescent dye-labeled nucleotides (probe molecules), the surface is coated with non-specific adsorption preventing molecules 507 having a negatively charged functional group. For example, the surface is coated with epoxy silane by the spin coating method, and the resulting surface is heated and then treated with a weak acidic solution (of pH about 5 to 6). Thus, an epoxy group is opened and an OH group is introduced to the surface, so as to provide a non-specific adsorption prevention effect.

The surfaces of microparticles 508 are preferably modified in advance with avidin 509. If gold or platinum microparticles are used, after reacting with amino thiol, the resulting microparticles are reacted with biotin-succinimide (NHS-Biotin manufactured by Pierce) and lastly with streptavidin, and thus, the microparticles can readily be modified with avidin. If the microparticles are made of a metal other than gold and platinum, the surfaces of the microparticles are oxidized by heating under oxygen atmosphere, and the resulting microparticles are reacted with aminosilane, then with biotin-succinimide (NHS-Biotin manufactured by Pierce), and ultimately with streptavidin. Thus, the surfaces of the metal microparticles can readily be modified with avidin. If semiconductor microparticles are used as microparticles 508, commercially available microparticles can be used. For example, microparticles available under a trade name of "Qdot® streptavidin label"

(manufactured by Invitrogen) having a diameter of 15 to 20 nm can be used. Alternatively, polystyrene beads can be used as microparticles 508. For example, polystyrene beads available under a trade name of "FluoroSpheres NeutrAvidin-Labeled" (manufactured by Invitrogen) having a diameter of 40 nm can be used. If an oligonucleotide is used as capture molecule 510, the oligonucleotide is synthesized to have a biotin-modified end, so that it can readily be immobilized on microparticle 508. The analysis device of this example can be produced by immobilizing, on each adhesive pad 503, each microparticle 508 on which the capture molecule 510 has been immobilized.

Example 6

Figure 6:
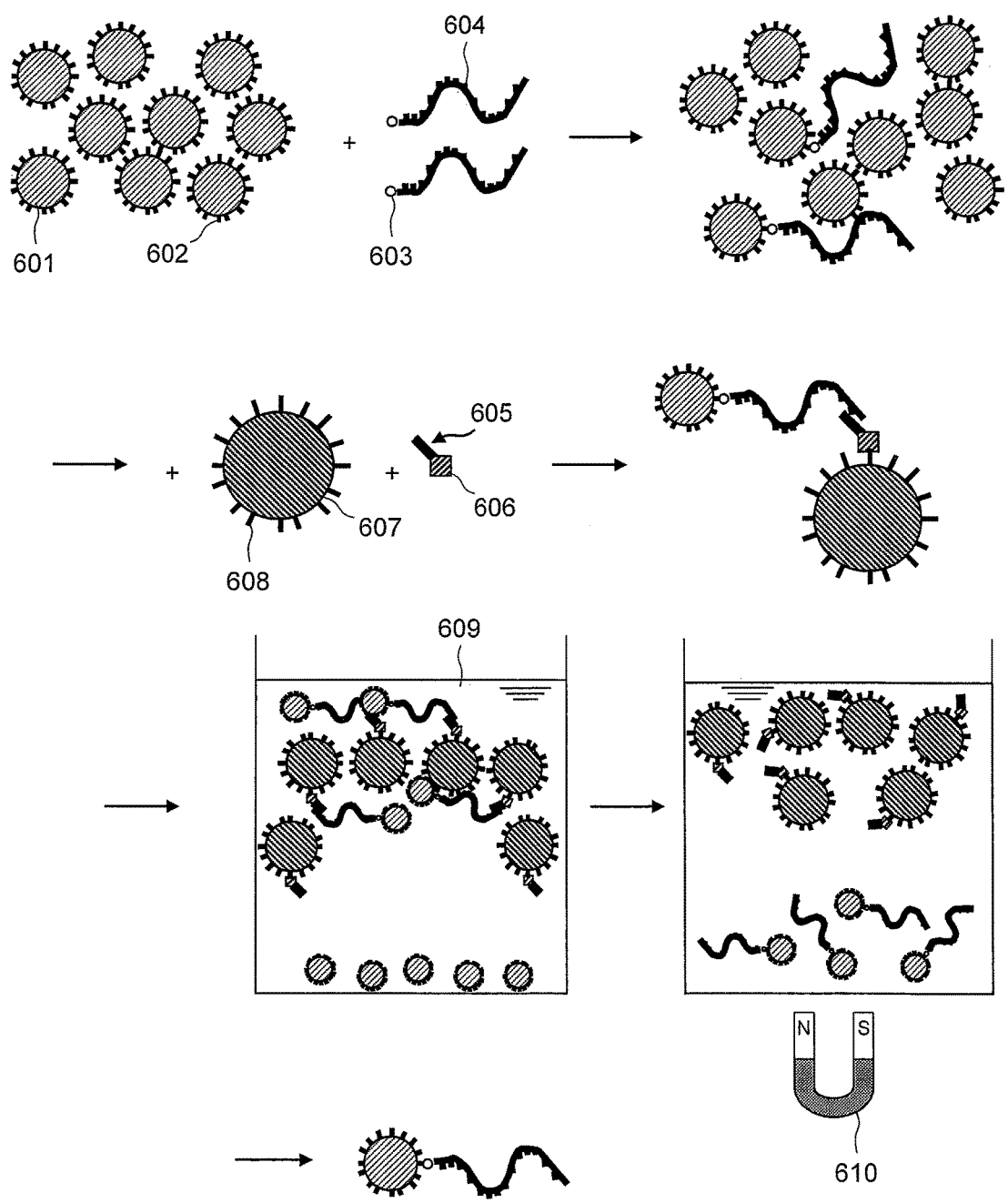
FIG. 6 is a diagram illustrating an exemplified method for producing a single-molecule immobilized microparticle used in one example.

In this example, a method for immobilizing one capture molecule on one microparticle in particular will be described with reference to FIG. 6 by taking, as an example, a method for producing a microparticle on which merely one capture molecule (that is preferably a nucleic acid if a biomolecule to be analyzed is a nucleic acid, or an antibody if the biomolecule is a protein) is immobilized. Binding site 602 for immobilizing capture molecule 604 is bound in advance to the surface of microparticle 601. As the binding site, for example, streptavidin can be used, and commercially available streptavidin-coated microparticles (manufactured by Invitrogen) can be used as the microparticles. Capture molecule 604 is modified in advance with binding site 603. As the binding site 603, a substance which readily binds to binding site 602 provided on the surface of microparticle 601 is selected. If the streptavidin is used as the binding site 602, for example, biotin is used as the binding site 603. Next, microparticles 601 and capture molecules 604 are reacted with each other, so as to bind capture molecules 604 to microparticles 601. In order to immobilize one capture molecule 604 on one microparticle 601, it is preferable to set the number of capture molecules 604 in unit volume to be smaller than the number of microparticles 601. If the capture molecules 604 are excessively present as compared with the microparticles 601, there is a high possibility that the number of capture molecules to be immobilized on one microparticle 601 is larger than one. As a result of studies carried out by the present inventors, if the reaction was performed with the number of microparticles 601 set to be ten times as large as the number of capture molecules 604, no capture molecules 604 were immobilized on each of approximately 90% of the microparticles 601, and merely one capture molecule 604 was immobilized on approximately 9% of the microparticles 601. This result is in accordance with results predicted by postulating Poisson distribution. Accordingly, if merely microparticles 601 having captured a capture molecule 604 are collected, then 90% or more of the collected microparticles 601 have only one capture molecule 604 immobilized on each microparticle 601.

If capture molecule 604 is a nucleic acid, then oligonucleotide 605 having a complementary sequence to the end sequence of capture molecule 604 and having an end modified with binding site 606 is prepared, and binding site 608 binding to the binding site 606 is coated in advance on the surface of collection microparticle 607. By using the thus prepared collection microparticle 607, microparticle 601 on which capture molecule 604 is immobilized can be bound to collection microparticle 607. As the collection method (trapping method), merely microparticles 601 on which capture molecules 604 are immobilized can be separated and collected for example, by binding capture molecule 604, in an aqueous solution 609, to collection microparticle 607 made of a polymer having a small specific weight, such as polypropylene, so that a microparticle 601 on which capture molecule 604 is immobilized can float but a microparticle 601 on which capture molecule 604 is not immobilized can sink to a lower portion of a vessel. In order to isolate microparticles 601 from collection microparticles 607, for example, a denature treatment (a high temperature treatment) for separating double strands of capture molecules 604 and oligonucleotides 605 can be employed. After separation, magnet 610 can be used for isolating the microparticles 601 on which the capture molecule 604 is immobilized.

If capture molecule 604 is an antibody, then oligonucleotide 605 having an aptamer sequence specifically binding to capture molecule 604 is prepared. Thus, in the same manner as in the above-described case where capture molecule 604 is a nucleic acid, the microparticles 601 on which capture molecules 604 are immobilized can be separated and collected at a rate as high as 90% or more by using collection microparticles 607. In order to isolate microparticles 601 from collection microparticles 607, for example, heat treatment to separate capture molecules 604 from oligonucleotides 605 of the aptamer can be employed.

Example 7

Figure 7:
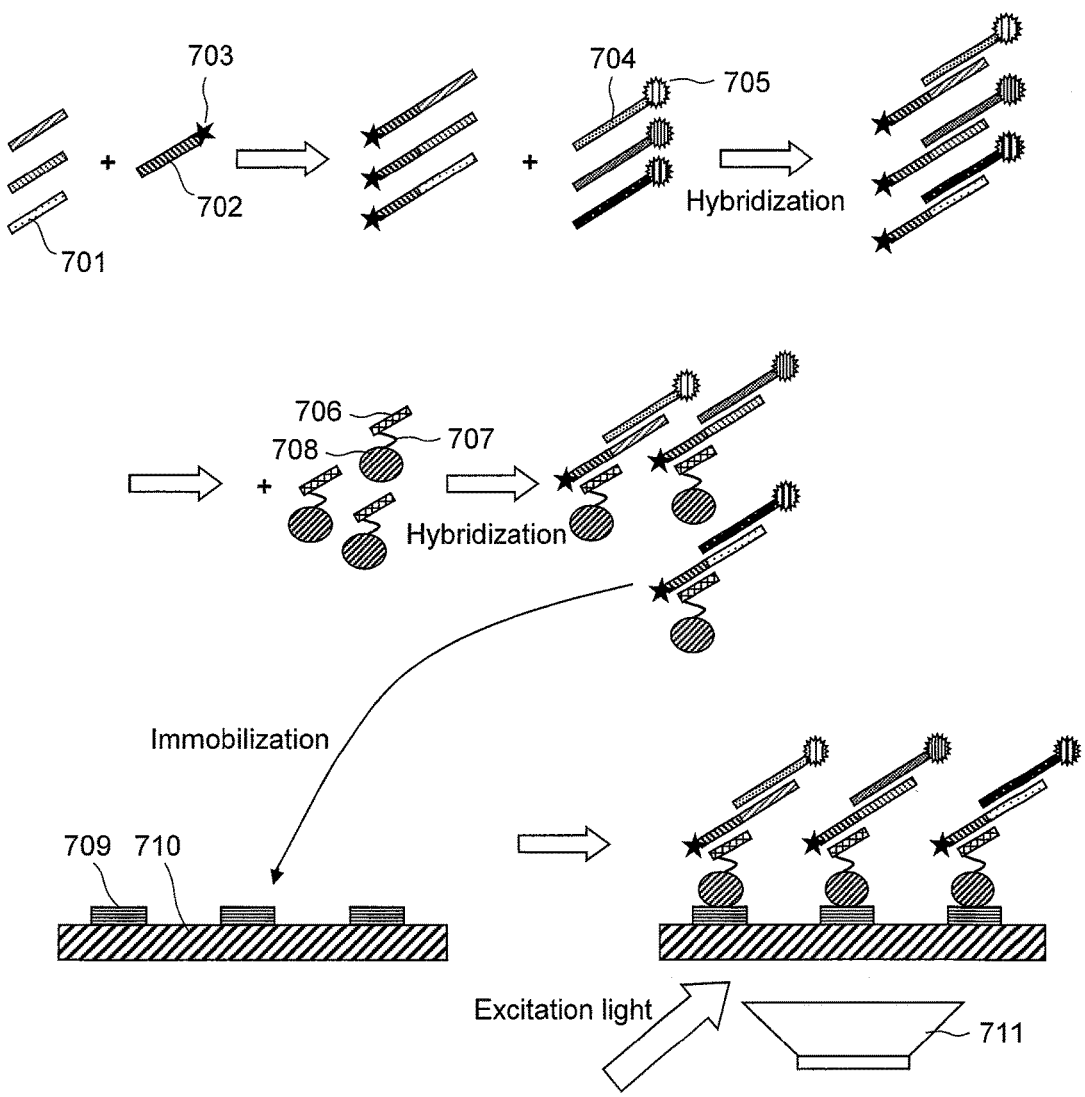
FIG. 7 is a diagram illustrating an exemplified analysis method of one example.

A device configuration and an analysis method of this example will be described with reference to FIG. 7. Capture tag molecule 702 labeled with fluorescent dye 703 is bound to nucleic acid fragment 701 to be analyzed. For the binding, a ligation reaction, or a coupling reaction between functional groups, with a functional group such as an amino group or a succinimide group introduced in advance into nucleic acid fragment 701 to be analyzed and capture tag molecule 702, can be employed. In particular, if the nucleic acid fragment 701 to be analyzed is a micro RNA, a method in which an RNA molecule having a length of 10 to 20 bases is used as capture tag molecule 702 and a T4RNA ligase is used for binding them is effectively employed. After binding capture tag molecule 702 labeled with fluorescent dye 703 to the nucleic acid fragment 701 to be analyzed, the resultant is hybridized with nucleic acid molecules (probe molecules) 704 labeled with fluorophores 705. Each nucleic acid molecule (probe molecules) 704 is used for identifying any of the nucleic acid fragments to be evaluated, and is necessary to have a nucleotide sequence representative of any of gene sequences. When designing sequences, it is necessary that individual labeled nucleic acid molecules (probe molecules) have a melting temperature, corresponding to a stability index of a nucleic acid double strand, falling in a prescribed range. The range is preferably smaller, and is preferably suppressed to approximately ±3° C. of a prescribed temperature. Further, the homology in the nucleotide sequence among the labeled nucleic acid molecules (probe molecules) is preferably lower, and the homology is suppressed preferably to 70% or less, and more preferably to 60% or less. Next, the method described in Example 6 is employed to prepare in advance microparticles 708 on each of which merely one capture molecule 706 is immobilized via a binding molecule 707. The hybridization is performed with the microparticles added, resulting in preparing the microparticles 708 on each of which a molecular pair of a hybrid of nucleic acid fragment 701 to be analyzed and nucleic acid molecule (probe molecule) 704 labeled with the fluorophore 705 is formed. Fluorescent beads containing fluorophores as described in Example 3 can be used as fluorophore 705.

Next, microparticles 708 having the hybrid thereon are immobilized on adhesive pads 709 having been formed on support substrate 710. As conditions for the immobilization reaction, those described in Example 3 may be employed.

Finally, fluorescence of fluorescent dye 703 and fluorophores 705 is detected by detector 711, so as to calculate the numbers of fluorescent light spots of fluorescent dye 703 and each type of fluorophores 705. The number of fluorescent light spots of fluorescent dye 703 corresponds to the total number of nucleic acid fragments 701 to be analyzed, and the number of fluorescent light spots of each type of fluorophores 705 corresponds to the number of each type of nucleic acid fragments. By thus counting the numbers of the light spots corresponding to all the nucleic acid fragments to be analyzed, the absolute number of biomolecules contained in the sample can be obtained. Further, by calculating the ratio between the absolute numbers thereof, the ratio of the number of nucleic acid fragments of each type to the total number of nucleic acid fragments to be analyzed can be calculated. The ratio thus calculated is particularly useful for comparative expression analysis between samples. For example, when searching for a marker gene having a different expression level between a healthy person and a patient having a specific disease, it is necessary to find a gene having an equivalent expression level in both samples to normalize the expression level. However, in actuality it is extremely difficult to find a gene having an equivalent expression level between samples. This difficulty is specifically reported in quantitative PCR (Nature Methods 2010, Vol. 7, pp. 687-692). By contrast, in the method of this example, the ratio of each type of biomolecule of interest to the whole sample can readily be calculated, and therefore, it is possible to directly compare a healthy person and a patient by comparing the ratios of each type of biomolecule to the whole biomolecules in the samples. This is particularly useful for comparative analysis of nucleic acid molecules in a clinical specimen.

Example 8

In Example 8, a method and a device configuration for remarkably improving the immobilization ratio of microparticles 803 each on which merely one capture molecule is immobilized will be described with reference to FIG. 8. In one method, a solution containing the microparticles 803 each on which merely one capture molecule is immobilized is dropped onto a support substrate 801 having adhesive pads 802 formed thereon, and the dropped solution is allowed to stand for a while to react therein while preventing the solution from drying out by providing a cover. In this case, microparticles 803 come close to adhesive pads 802 in a probabilistic manner due to Brownian movement. When, for example, the surfaces of adhesive pads 802 are covered with alkane molecules used as binding molecules so as to attain intermolecular force with microparticles 803 made of a polymer such as polystyrene, microparticle 803 rapidly binds to adhesive pad 802 merely by bringing it close to adhesive pad 802, and a microparticle thus adhered never peels off. In order to accelerate further active collision, the collision frequency of microparticles 803 against adhesive pads 802 can be increased by, for example, stirring the solution with a stirrer or causing convection in the solution by heating or applying microwaves. As an effective method for further positively increasing the collision frequency of microparticles 803, the solution containing microparticles 803 is stirred in a channel. This method will be described with reference to FIG. 8. First, as illustrated in FIG. 8A, a channel is provided on support substrate 801, and irregular plate 804 (concave and convex plate 804) having grooves as illustrated in FIG. 8B is used as a cover for the channel. Quartz or PDMS (polydimethylsiloxane) having been subjected to the non-specific adsorption prevention treatment with a silane coupling agent or the like is preferably used as the material of the channel. In general, when a solution is allowed to flow in a minute channel in a prescribed direction, the solution passes through the channel in the form of a laminar flow. Therefore, merely microparticles 803 present in a layer close to the support substrate 801 are immobilized on the adhesive pads 802, and microparticles 803 present in a layer away from the support substrate 801 cannot come close to the support substrate 801. For example, if microparticles 803 are to be adsorbed by the intermolecular force onto adhesive pads 802 in a standing state or in a laminar flow, then, since the potential energy is in inverse proportion to the sixth power of the distance, merely microparticles 803 present in the vicinity of support substrate 801, specifically, in positions away from it by several tens of μm at most, have the opportunity to collide. Since the collision frequency of microparticles 803 against the adhesive pads is in proportion to the concentration of microparticles 803, most microparticles 803 of the surface layer close to support substrate 801 are immobilized on adhesive pads 802 after a certain period of time. Therefore, migration of microparticles 803 between layers is through diffusion alone, and a concentration difference occurs between the portion close to the surface layer and other layer(s), and hence, the substantial concentration of microparticles 803 with respect to adhesive pads 802 is significantly lowered.

Figure 8:
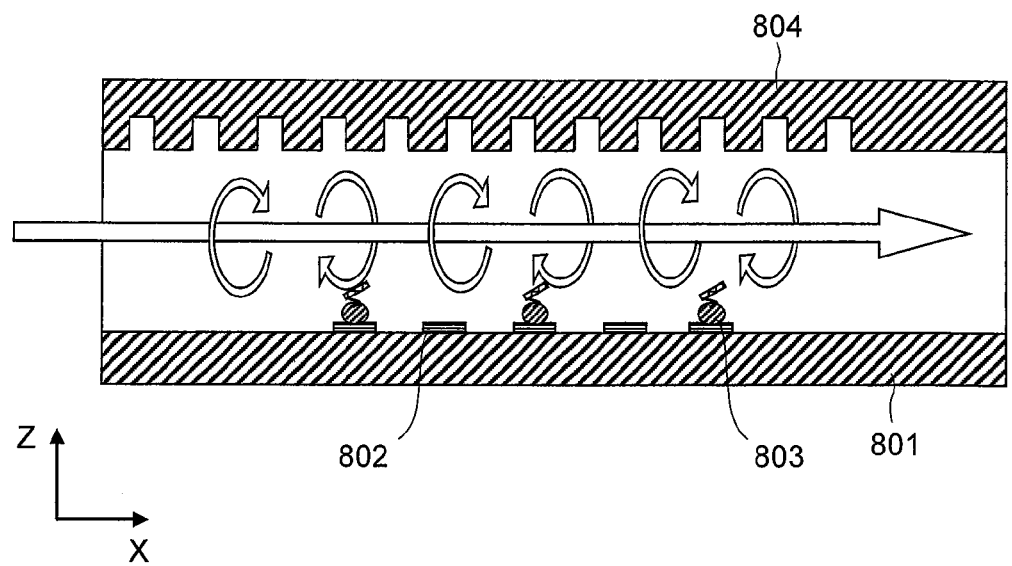
FIG. 8 is a diagram illustrating exemplified method and device for producing a microparticle on which a single capture molecule is immobilized.
Figure 8:
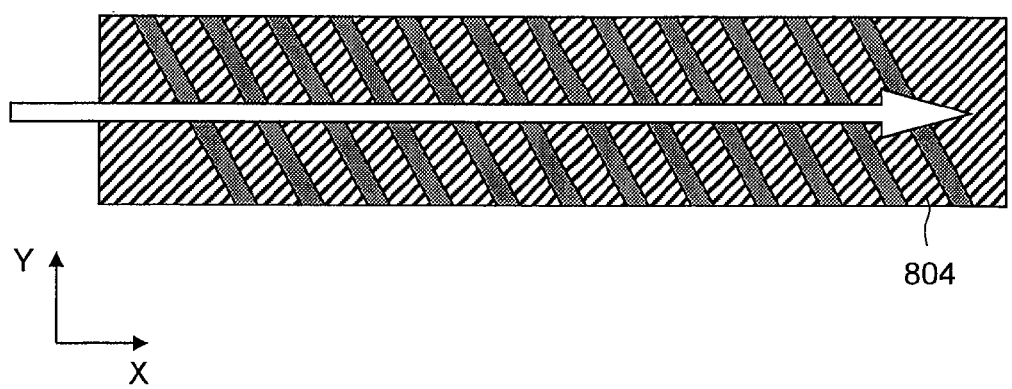

Accordingly, irregular plate 804 as illustrated in FIG. 8B is provided along the flowing direction of the fluid. In the case exemplified in FIG. 8, the plate is disposed to oppose support substrate 801. While the fluid flowing in the prescribed direction is passing irregular plate 804, a vortex having an axis in the X-direction or a turbulent flow is caused, and hence the fluid moves also in the Z-axis direction. The flow depends upon the shape of the irregular plate 804. An example of such a phenomenon is described in Science 2002, Vol. 295, pp. 647-650.

By causing the vertical flow in the aforementioned manner, the collision frequency of microparticles 803 contained in the solution against adhesive pads 802 can be significantly increased. At the same time, as compared with the method in which the reaction is caused by allowing the solution to stand still on support substrate 801, the time can be significantly shortened. In general, the diffusion speed of microparticles of μm in diameter is 0.1 to 1 μm/sec, but if the solution is allowed to flow at a rate of 200 μm/sec with the irregular plate 804 of FIG. 8B provided, a flow of approximately 10 μm/sec occurs in the Z-axis direction. Accordingly, as compared with the case of standing still, the reaction speed is improved theoretically by approximately 10 to 100 times. Further, if the inlet and the outlet of a channel are connected via a tube by using a diaphragm pump or the like as a reaction chamber, the fluid flows not only in the prescribed direction but in directions converted at a certain period, and hence, even slight amounts of the fluid can be repeatedly stirred. Here, it is preferable that the thickness of the solution on the support substrate 801 having the adhesive pads 802 thereon is smaller, thereby further increasing the collision frequency. If $10^5$ biomolecules (namely, microparticles) are to be reacted with $10^6$ adhesive pads in a reaction chamber with a length of 10 mm, a width of 5 mm and a height of 1 mm, according to calculations, then approximately 50% of the biomolecules are immobilized on the adhesive pads by allowing the solution to make 15 reciprocating movements at a rate of 200 μm/sec. In order to further immobilize approximately 95% of the biomolecules (namely, the microparticles), about 100 reciprocating movements are required, which takes approximately 80 minutes. When a similar flow was actually caused approximately 10 times, the reaction efficiency was increased about 30% as compared with the case where the reaction was caused in a standing state. The stirring can not only be employed for increasing the immobilization ratio of the microparticles 803 but also be similarly employed for increasing the efficiency of the hybridization of the biomolecules to be analyzed with the capture molecules or the hybridization of fluorophore-labeled nucleic acid molecules (probe molecules) used for detection and the biomolecules to be analyzed.

Example 9

Figure 9:
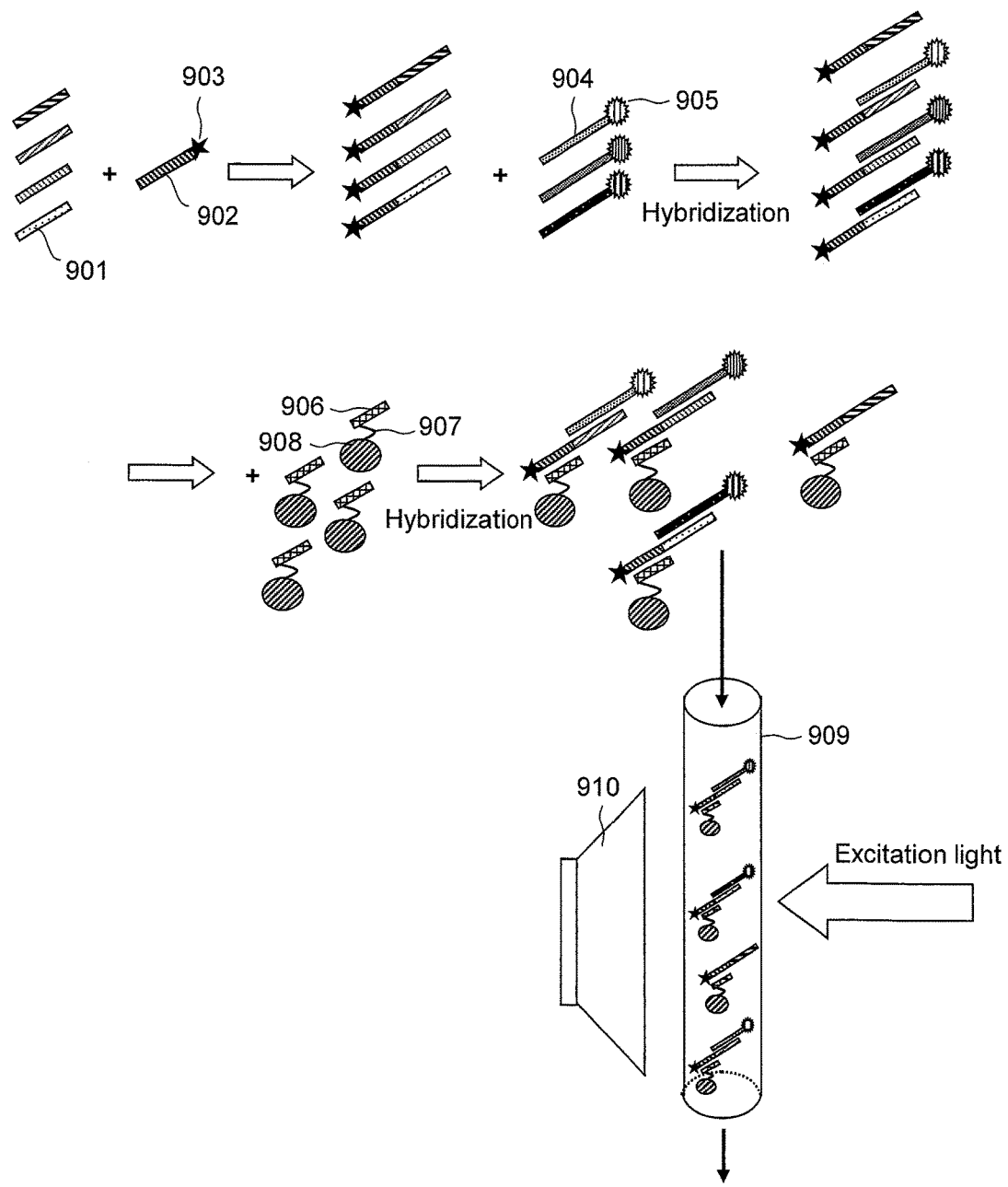
FIG. 9 is a diagram illustrating an exemplified analysis method of one example.

An analysis method of this example will be described with reference to FIG. 9. A capture tag molecule 902 labeled with a fluorescent dye 903 is bound to a nucleic acid fragment 901 to be analyzed. For the binding, it is possible to employ a ligation reaction, or a coupling reaction between functional groups wherein functional group such as an amino group and a succinimide group are introduced in advance to nucleic acid fragment 901 to be analyzed and capture tag molecule 902 and these may be coupled. In particular, if the nucleic acid fragments 901 to be analyzed are a micro RNA, then a binding method in which an RNA molecule having a length of 10 to 20 bases is used as capture tag molecule 902 and a T4RNA ligase is used for binding the same is effective. After binding capture tag molecule 902 labeled with fluorescent dye 903 to the nucleic acid fragment 901 to be analyzed, the resultant is hybridized with nucleic acid molecules (probe molecules) 904 labeled with fluorophores 905. Each nucleic acid molecule (probe molecule) 904 is used for identifying any of the nucleic acid fragments to be evaluated, and is necessary to have a nucleotide sequence representative of any of gene sequence. When designing sequences, it is necessary that individual labeled nucleic acid molecules (probe molecules) have a melting temperature, which serves as a stability index of a nucleic acid double strand, falling in a certain range. The range is preferably smaller, and is preferably suppressed to approximately ±3° C. of a prescribed temperature. Further, the homology in the nucleotide sequence among the labeled nucleic acid molecules (probe molecules) is preferably lower, and the homology is suppressed preferably to 70% or less, and more preferably to 60% or less. Then, the method described in Example 6 is employed to prepare in advance microparticles 908 on each of which merely one capture molecule 906 is immobilized via a binding molecule 907. The hybridization is performed by adding the microparticles, resulting in preparing the microparticles 908 on each of which a molecular pair of a hybrid of the nucleic acid fragment 901 to be analyzed and the nucleic acid molecule 904 labeled with the fluorophore 905 is formed. As fluorophore 905, fluorescent beads containing fluorophores can be used as described in Example 1.

Next, microparticles 908 having the hybrid thus formed are allowed to flow through channel 909 and irradiated with excitation light, so as to detect intensities of fluorescence of fluorescent dye 903 and fluorescence intensity of each fluorophore 905 by detector 910. It is preferable to set the diameter of channel 909 not to be larger than twice the diameter of microparticle 908 because simultaneous measurement of fluorescence of multiple fluorescent dyes 903 can be thus avoided, and fluorescence can be measured distinguishing each microparticle 908. The number of fluorescent light spots of fluorescent dye 903 is counted so as to obtain a value corresponding to the total number of nucleic acid fragments. On the other hand, only when the fluorescence of fluorescent dye 903 and the fluorescence of fluorophore 905 are simultaneously measured should the number of light spots of a specific fluorophore be counted in order to obtain a value corresponding to the number of corresponding type of nucleic acid fragment. The absolute number of the nucleic acid fragments can be obtained by calculating the light spots of all the fluorophores. By calculating the ratio of the absolute numbers, the ratio(s) of the number of each type of nucleic acid fragments to the total number of nucleic acid fragments of the sample can be calculated. In the method of this example, the expression level of each gene can be obtained as the ratio in the expression level to the expression level of all the genes, and therefore, comparison between different samples, for example, a sample of a healthy person and a sample of a patient, can be directly performed. This is particularly useful for comparative analysis of nucleic acid molecules in a clinical specimen.

As microparticles 908, it is possible to use microparticles of a polymer such as polystyrene, and it is possible to use magnetic microparticles containing, in a polymer, a magnetic metal powder. In particular, if magnetic microparticles are used, before allowing microparticles 908 to flow through channel 909 after the reaction, unreacted portions of capture tag molecules 902 labeled with fluorescent dye 903 and nucleic acid molecules (probe molecules) 904 labeled with fluorophores 905, which are not immobilized on microparticles 908 but remain in the reaction solution, can readily be removed. This leads to a major advantage that the measurement can readily be performed in counting the light spots of a specific fluorophore merely when the fluorescence of fluorescent dye 903 and the fluorescence of fluorophore 905 are simultaneously measured.

Example 10

Figure 10:
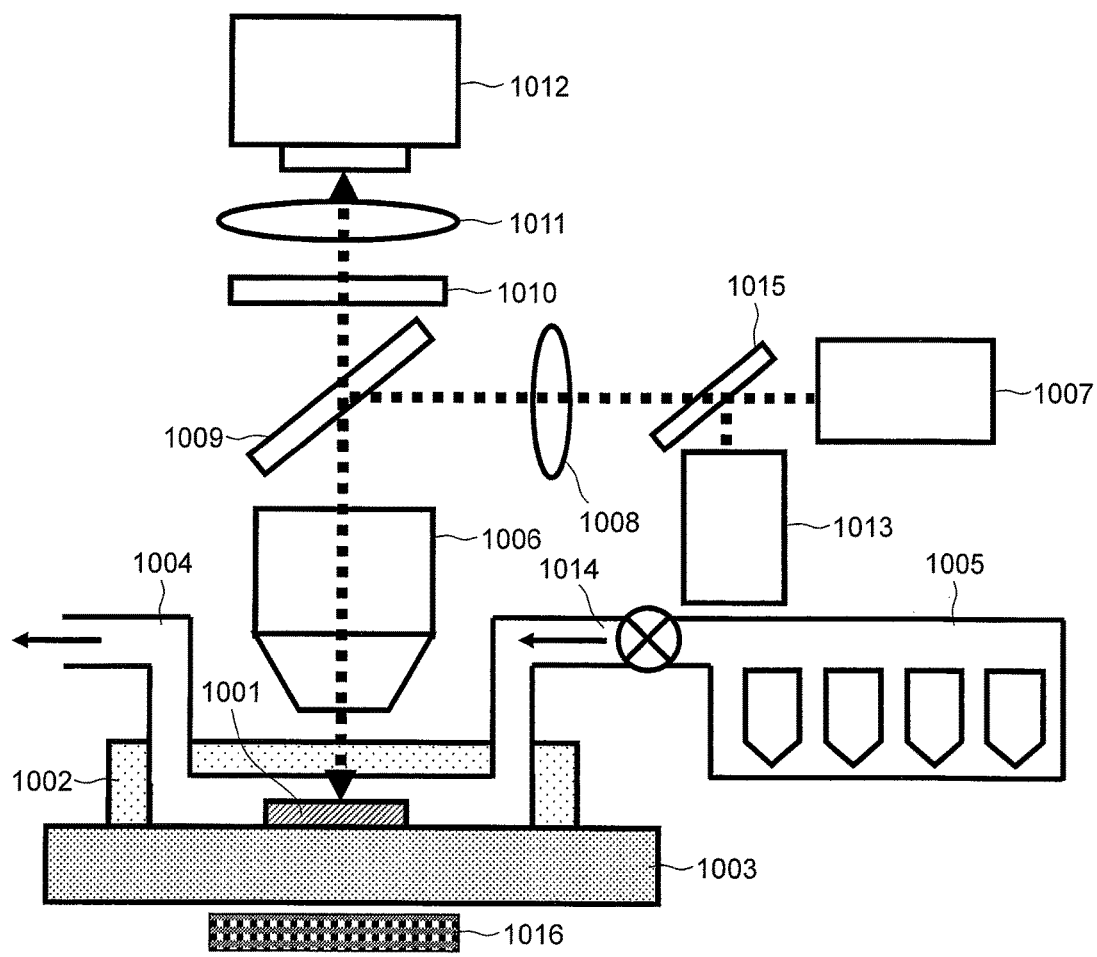
FIG. 10 is a diagram illustrating an exemplified biomolecule analyzer of one example.

In this example, an exemplified preferable configuration of a biomolecule analyzer used in a method for analyzing biomolecules will be described with reference to FIG. 10 by taking, as an example, a case where the biomolecules are nucleic acids.

A nucleic acid analyzer of this example comprises: means for supplying, to a nucleic acid analysis device substrate, a nucleic acid sample solution, a fluorophore-labeled molecule solution and a washing solution; temperature adjusting means for performing hybridization in a reaction chamber; means for irradiating the nucleic acid analysis device substrate with light; and emission detecting means for measuring fluorescence of a fluorophore of a fluorophore-labeled molecule. More specifically, the reaction chamber is formed by placing nucleic acid analysis device substrate 1001 on temperature adjustment plate 1003, and adhering, onto temperature adjustment plate 1003, channel member 1002 having channel 1004. Channel member 1002 is made of, for example, PDMS (polydimethylsiloxane).

Solution feeding unit 1005 is connected to inlet 1014, so that a nucleic acid sample solution, a fluorophore-labeled molecule solution and a washing solution stored in the solution feeding unit 1005 can be successively supplied to the reaction chamber disposed on the nucleic acid analysis device substrate 1001. After supplying the nucleic acid sample solution and the fluorophore-labeled molecule solution to the reaction chamber, these solutions are held in the reaction chamber disposed on nucleic acid analysis device substrate 1001 within channel 1004, and the hybridization is performed by temperature adjustment plate 1003 in a temperature range from 30° C. to 80° C. After the hybridization, magnetic microparticles present in the reaction chamber are collected and immobilized by magnet unit 1016 on nucleic acid analysis device substrate 1001, and then, the washing solution is supplied from solution feeding unit 1005 to the reaction chamber for washing unreacted substances.

After washing, fluorescence detection is performed. Depending on the types of fluorophores to be used, an appropriate excitation light source may be selected. If, for example, Cy5, Cy5.5 and Cy3 are used as fluorophores contained in fluorescent beads, two types of excitation light of wavelengths of 532 nm (YAG laser) and 633 nm (He—Ne laser) may be employed. Laser light oscillated from a YAG laser light source 1007 (of a wavelength of 532 nm and output of 20 mW) and an He—Ne laser light source 1013 (of a wavelength of 633 nm and output of 20 mW) is adjusted to be coaxial with each other by dichroic mirror 1015, the resultant light is allowed to pass through lens 1008, and is introduced to an objective lens 1006 by dichroic mirror 1009, so as to irradiate the nucleic acid analysis device substrate 1001. Fluorescence emitted from the fluorophore-label molecules travels on the coaxial light path in the reverse direction to the excitation light, specifically, is collected by objective lens 1006, passes through dichroic mirror 1009, and is imaged on a photosensitive surface of two-dimensional CCD camera 1012 by imaging lens 1011. Scattered light of the excitation light is removed by optical filter 1010.

By assembling the nucleic acid analyzer using the solution feeding unit, the temperature adjustment plate, the excitation light sources and the fluorescence detecting unit as described above, it is possible to automate the analysis of nucleic acids by hybridization, and thus, the throughput can be remarkably improved as compared with those attained by conventional techniques.

Further, even when the biomolecules are proteins, the analysis can be performed by using an analyzer having a similar configuration.

REFERENCE SIGNS LIST 101 nucleic acid fragment to be analyzed
102 capture tag
103 fluorescent dye
104 nucleic acid molecule (probe molecule)
105 fluorophore
106 capture molecule
107 binding molecule
108 magnetic microparticle
109 magnet
110 support substrate
111 detector
201 magnetic microparticle
202 antibody
203 binding molecule
204 protein to be analyzed
205 fluorescent labeled antibody (probe molecule)
206 support substrate
207 magnet
208 detector
301 support substrate
302 adhesive pad
303 microparticle
304 capture molecule
305 binding molecule
306 nucleic acid fragment (biomolecule) to be analyzed
307 capture tag molecule
308 fluorophore-labeled nucleic acid molecule (probe molecule)
401 support substrate
402 adhesive pad
403 microparticle
404 capture molecule
405 linear molecule
406 functional group
407 functional group
501 smooth support substrate
502 electron beam positive resist
503 adhesive pad
504 linear molecule
505, 506 functional group at end of linear molecule
507 non-specific adsorption preventing molecule
508 microparticle
509 avidin
510 capture molecule
601 microparticle
602 binding site
603 binding site
604 capture molecule
605 oligonucleotide
606 binding site
607 collection microparticle
608 binding site
609 aqueous solution
610 magnet
701 nucleic acid fragment to be analyzed
702 capture tag molecule
703 fluorescent dye
704 nucleic acid molecule (probe molecule)
705 fluorophore
706 capture molecule
707 binding molecule
708 microparticle
709 adhesive pad
710 support substrate
711 detector
801 support substrate
802 adhesive pad
803 microparticle
804 irregular plate (concave and convex plate)
901 nucleic acid fragment to be analyzed
902 capture tag molecule
903 fluorescent dye
904 nucleic acid molecule (probe molecule)
905 fluorophore
906 capture molecule
907 binding molecule
908 microparticle
909 channel
910 detector
1001 nucleic acid analysis device substrate
1002 channel member
1003 temperature adjustment plate
1004 channel
1005 solution feeding unit
1006 objective lens
1007 YAG laser light source 1008 lens
1009 dichroic mirror
1010 optical filter
1011 imaging lens
1012 two-dimensional CCD camera
1013 He—Ne laser light source
1014 inlet
1015 dichroic mirror
1016 magnet unit

The invention claimed is:

1. A method for analyzing biomolecules, comprising the steps of:
   immobilizing biomolecules to be analyzed on surfaces of magnetic microparticles;
   reacting fluorophore-labeled probe molecules with the biomolecules to be analyzed;
   after the step of immobilizing the biomolecules to the surfaces of magnetic microparticles and after the step of reacting fluorophore-labeled probe molecules with the biomolecules, collecting and immobilizing the magnetic microparticles in a single layer on a surface of a support substrate, wherein the magnetic microparticles directly contact the support substrate; and
   measuring the fluorophore labels on the support substrate,
   wherein the steps of collecting and immobilizing the magnetic particles in a single layer on the surface of the support substrate include applying a magnetic field by a single magnet that is disposed on an opposite side of the substrate than a side of the substrate having the surface that the magnetic particles contact,
   wherein the magnetic microparticles have a size of 1 μm or less,
   wherein the surface of the support substrate is a flat smooth surface on which the magnetic microparticles are collected and immobilized,
   wherein one molecule of the biomolecules to be analyzed is immobilized per magnetic microparticle, and
   wherein measuring of the labels includes observing single molecule fluorescence of the biomolecules by counting light spots.

2. The method for analyzing biomolecules according to claim 1, wherein capture molecules are immobilized in advance on the surfaces of the magnetic microparticles, and then the biomolecules to be analyzed are immobilized on the surfaces of the magnetic microparticles via the capture molecules.

3. The method for analyzing biomolecules according to claim 1, wherein one capture molecule is immobilized in advance per magnetic microparticle, and the biomolecules to be analyzed are immobilized on the surfaces of the magnetic microparticles via the capture molecules.

4. The method for analyzing biomolecules according to claim 1, wherein the step of reacting the fluorophore-labeled probe molecules with the biomolecules to be analyzed is performed after the step of immobilizing the biomolecules to be analyzed on the surfaces of magnetic microparticles.

5. The method for analyzing biomolecules according to claim 1, wherein the step of immobilizing biomolecules to be analyzed on the surfaces of magnetic microparticles is performed after the step of reacting the fluorophore-labeled probe molecules with the biomolecules to be analyzed.

6. The method for analyzing biomolecules according to claim 1, wherein the fluorescent labels are labeled probe molecules with multiple types of fluorophores mixed in different ratios depending on the types of biomolecules to be measured.

7. The method for analyzing biomolecules according to claim 1, wherein the fluorescent labels are labeled probe molecules with fluorophores emitting fluorescence in different colors depending on the types of biomolecules to be measured.

8. The method for analyzing biomolecules according to claim 1, further comprising the step of adding a common label to the biomolecules to be analyzed,
   wherein probe molecules labeled with a label different from the common label are reacted with the biomolecules to be analyzed in order to calculate the ratio between the common label and the different label, and the quantity of reacted biomolecules in the total quantity of the biomolecules to be analyzed is evaluated based on the ratio.

9. The method for analyzing biomolecules according to claim 1, wherein the biomolecules are nucleic acids.

10. The method for analyzing biomolecules according to claim 9, wherein the probe molecules are nucleic acids hybridizable with the biomolecules to be measured.

11. The method for analyzing biomolecules according to claim 1, wherein the biomolecules are proteins.

12. The method for analyzing biomolecules according to claim 11, wherein the probe molecules are antibodies to the biomolecules to be measured.

13. The method for analyzing biomolecules according to claim 1, further comprising:
    evaluating an absolute concentration of the biomolecules to be analyzed based on a result of measuring the labels on the support substrate.

14. A method for analyzing biomolecules, comprising the steps of:
    binding a plurality of capture molecules to respective surfaces of a plurality of magnetic microparticles wherein one capture molecule is immobilized per one magnetic microparticle;
    immobilizing individual biomolecules to be analyzed on surfaces of the magnetic microparticles via the one capture molecule of each of the magnetic microparticles;
    reacting fluorophore-labeled probe molecules with the individual biomolecules to be analyzed;
    after the step of immobilizing the individual biomolecules to the surfaces of the plurality of magnetic microparticles and after the step of reacting fluorophore-labeled probe molecules with the biomolecules, collecting and immobilizing the magnetic microparticles in a single layer on a surface of a support substrate, wherein the magnetic microparticles directly contact the support substrate; and
    measuring fluorophore labels on the support substrate,
    wherein the magnetic microparticles have a size of 1 μm or less,
    wherein the surface of the support substrate is a flat smooth surface on which the magnetic microparticles are collected and immobilized, and
    wherein measuring of the labels includes observing single molecule fluorescence of the biomolecules by counting light spots.

15. The method for analyzing biomolecules according to claim 14,
    wherein the plurality of magnetic microparticles are greater than the plurality of capture molecules.

16. The method for analyzing biomolecules according to claim 15, wherein a number of the plurality of magnetic microparticles is at least ten times a number of the plurality of capture molecules.

17. The method for analyzing biomolecule according to claim 14,
  wherein the steps of collecting and immobilizing the magnetic particles in the single layer on the surface of the support substrate include applying a magnetic field by a single magnet that is disposed on an opposite side of the substrate than a side of the substrate having the surface that that the magnetic particles contact.

\* \* \* \* \*